(12) United States Patent
Walters

(10) Patent No.: US 9,995,623 B2
(45) Date of Patent: Jun. 12, 2018

(54) AMBIENT LIGHT ASSISTED SPECTROSCOPY

(71) Applicant: Integrated Plasmonics Corporation, San Francisco, CA (US)

(72) Inventor: Robert Joseph Walters, San Francisco, CA (US)

(73) Assignee: INTEGRATED PLASMONICS CORPORATION, San Francisco, CA (US)

( * ) Notice: Subject to any disclaimer, the term of this patent is extended or adjusted under 35 U.S.C. 154(b) by 0 days. days.

(21) Appl. No.: 14/775,299

(22) PCT Filed: Dec. 3, 2013

(86) PCT No.: PCT/US2013/072936
§ 371 (c)(1),
(2) Date: Sep. 11, 2015

(87) PCT Pub. No.: WO2014/143235
PCT Pub. Date: Sep. 18, 2014

(65) Prior Publication Data
US 2016/0033328 A1 Feb. 4, 2016

Related U.S. Application Data

(60) Provisional application No. 61/785,335, filed on Mar. 14, 2013.

(51) Int. Cl.
*G01J 3/28* (2006.01)
*G01J 3/02* (2006.01)
(Continued)

(52) U.S. Cl.
CPC ............. *G01J 3/0208* (2013.01); *G01J 3/027* (2013.01); *G01J 3/0216* (2013.01);
(Continued)

(58) Field of Classification Search
CPC .... G01J 3/02; G01J 3/18; G01J 3/2803; G01J 3/2823; G01J 3/28
(Continued)

(56) References Cited

U.S. PATENT DOCUMENTS 4,516,857 A 5/1985 Preston et al.
4,659,222 A 4/1987 Ekholm
(Continued)

FOREIGN PATENT DOCUMENTS

EP 1 217 426 A1 6/2002
WO 1998/034098 A1 8/1998
(Continued)

OTHER PUBLICATIONS

U.S. Appl. No. 14/095,971, filed Dec. 3, 2013.
(Continued)

*Primary Examiner* — Md M Rahman
(74) *Attorney, Agent, or Firm* — Chen Yoshimura LLP

(57) ABSTRACT

A spectroscopic device, which may be a handheld spectroscopic light source, which uses ambient light as a primary broadband light source, but which may be supplemented with an auxiliary light source to supplement band regions which may be deficient in the broad band source. The spectroscopic device makes use of a number of parallel control channels to monitor for sufficient light and to compensate for variations in the input light levels.

12 Claims, 8 Drawing Sheets

(51) Int. Cl.
| | |
|---|---|
| *G01J 3/10* | (2006.01) |
| *G01N 21/25* | (2006.01) |
| *G01J 3/12* | (2006.01) |
| *G01J 3/18* | (2006.01) |
| *G01J 3/42* | (2006.01) |
| *G01N 21/31* | (2006.01) |

(52) U.S. Cl.
CPC ............ *G01J 3/0224* (2013.01); *G01J 3/0229* (2013.01); *G01J 3/0264* (2013.01); *G01J 3/0272* (2013.01); *G01J 3/0289* (2013.01); *G01J 3/10* (2013.01); *G01J 3/12* (2013.01); *G01J 3/18* (2013.01); *G01J 3/2803* (2013.01); *G01J 3/42* (2013.01); *G01N 21/255* (2013.01); *G01J 2003/1213* (2013.01); *G01N 2021/3122* (2013.01)

(58) Field of Classification Search
USPC .......................................................... 356/328
See application file for complete search history.

(56) References Cited

U.S. PATENT DOCUMENTS

| | | | |
|---|---|---|---|
| 5,071,248 A * | 12/1991 | Tiefenthaler | G01N 21/431 356/128 |
| 5,116,759 A | 5/1992 | Klainer et al. | |
| 5,644,512 A | 7/1997 | Chernoff et al. | |
| 5,674,457 A | 10/1997 | Williamsson et al. | |
| 5,747,809 A * | 5/1998 | Eckstrom | G01N 21/3504 250/339.13 |
| D433,150 S | 10/2000 | Wahlqvist et al. | |
| 6,838,650 B1 | 1/2005 | Toh | |
| 7,466,409 B2 | 12/2008 | Scherer et al. | |
| 8,076,128 B2 | 12/2011 | Liederman et al. | |
| 8,231,268 B2 | 7/2012 | Krol et al. | |
| 8,284,401 B2 | 10/2012 | Choi et al. | |
| 2005/0114332 A1 | 5/2005 | Lee et al. | |
| 2006/0034729 A1 | 2/2006 | Poponin | |
| 2007/0070347 A1 | 3/2007 | Scherer et al. | |
| 2008/0135739 A1 | 6/2008 | Kim et al. | |
| 2008/0180692 A1* | 7/2008 | Goh | G01N 33/54373 356/521 |
| 2010/0039648 A1 | 2/2010 | Garcia da Fonseca | |
| 2010/0046060 A1 | 2/2010 | Lee et al. | |
| 2010/0097612 A1* | 4/2010 | Utsunomiya | G01N 21/554 356/445 |
| 2010/0157306 A1 | 6/2010 | Choi et al. | |
| 2011/0085167 A1 | 4/2011 | Guan et al. | |
| 2011/0108720 A1* | 5/2011 | Ford | E21B 49/08 250/262 |
| 2011/0111487 A1 | 5/2011 | Goh et al. | |
| 2012/0225475 A1 | 9/2012 | Wagner et al. | |
| 2014/0176939 A1 | 6/2014 | Shah | |

FOREIGN PATENT DOCUMENTS

| | | |
|---|---|---|
| WO | 2006/009724 A2 | 1/2006 |
| WO | 2011/106057 A2 | 9/2011 |
| WO | 2012/054351 A2 | 4/2012 |
| WO | 2014/089120 A1 | 6/2014 |
| WO | 2014/123613 A1 | 8/2014 |
| WO | 2014/143234 A1 | 9/2014 |
| WO | 2014/158248 A1 | 10/2014 |

OTHER PUBLICATIONS

U.S. Appl. No. 14/648,843, filed Jun. 1, 2015.
U.S. Appl. No. 14/766,551, filed Aug. 7, 2015.
U.S. Appl. No. 14/775,266, filed Sep. 11, 2015.
U.S. Appl. No. 14/774,990, filed Sep. 11, 2015.
International Search Report (ISR) issued in PCT/US2013/072927 dated Apr. 2014.
Written Opinion (PCT/ISA/237) issued in PCT/US2013/072927 dated Apr. 2014.
Huang et al., "Micro-hole drilling with femtosecond fiber laser", SPIE Paper No. 8607-19, Photonics West 2013, Feb. 2-7, 2013.
International Search Report (ISR) issued in PCT/US2013/072929 dated Apr. 2014.
Written Opinion (PCT/ISA/237) issued in PCT/US2013/072929 dated Apr. 2014.
International Search Report (ISR) issued in PCT/US2013/072930 dated Apr. 2014.
Written Opinion (PCT/ISA/237) issued in PCT/US2013/072930 dated Apr. 2014.
International Search Report (ISR) issued in PCT/US2013/072932 dated Apr. 2014.
Written Opinion (PCT/ISA/237) issued in PCT/US2013/072932 dated Apr. 2014.
International Search Report (ISR) issued in PCT/US2013/072936 dated Apr. 2014.
Written Opinion (PCT/ISA/237) issued in PCT/US2013/072936 dated Apr. 2014.
Fiedler, "Incoherent Broad-Band Cavity-Enhanced Absorption Spectroscopy", 2005, Berlin.
Barron, "Basics of UV-Visible Spectroscopy", Physical Methods in Chemistry and Nano Science, Jun. 5, 2010.
Chen et al., "A CMOS Image Sensor Integrated with Plasmonic Colour Filters", Plasmonics, Dec. 2012, vol. 7, Issue 4, (abstract) Springer Link.
Mansuripur et al., "Plasmonic nano-structures for optical data storage", Optics Express, Aug. 3, 2009, vol. 17, No. 16, pp. 14001-14014.
Genet et al., "Light in tiny holes", nature, Jan. 4, 2007, vol. 445, pp. 39-46.
Koerkamp et al., "Strong Influence of Hole Shape on Extraordinary Transmission through Periodic Arrays of Subwavelength Holes", Physical Review Letters, May 7, 2004, vol. 92, No. 18, pp. 183901-1-183901-4.
Jones et al., "Surface Plasmon assisted extraordinary transmission in metallic nanohole arrays and its suitability as a bio-sensor", Journal of Physics: Conference Series 307, IOP Publishing, 2011, pp. 1-7.
Tok et al., "Unidirectional broadband radiation of honeycomb plasmonic antenna array with broken symmetry", Optics Express, Nov. 7, 2011, vol. 19, No. 23, pp. 22731-22742.
Pacifici et al., "Universal optical transmission features in periodic and quasiperiodic hole arrays", Optics Express, Jun. 9, 2008, vol. 16, No. 12, pp. 9222-9238.
Singh et al., "Surface Plasmon Resonance Enhanced Transmission of Light through Gold-Coated Diffraction Gratings", Analytical Chemistry, May 15, 2008, vol. 80, No. 10, pp. 3803-3810.

* cited by examiner

AMBIENT LIGHT ASSISTED SPECTROSCOPY

BACKGROUND

Field of the Invention

The present disclosure relates to spectroscopic and other instrumentations and methods relying at least in part on ambient light as a light source for enabling biological and chemical sensing capable of detecting minute quantities of biological or chemical substances.

Description of the Related Art

It is to be understood that both the foregoing general description and the following detailed description are exemplary and explanatory, and are intended to provide further explanation of the invention as claimed in a patent(s) originating from this application.

Spectrometers measure properties of light over a portion of the electromagnetic spectrum. Spectrometers usually employ a source of electromagnetic energy, and various optical devices such as mirrors and gratings as optical filters for dispersing the light to the detector, as well as a detector to detect the light intensity as a function of wavelength. Spectrometers are used to detect and quantify the characteristics or concentration of a physical, chemical or biological target object. Medical diagnostic machines using optical spectrometers allow for characterization of chemical and biological information that can be used to detect disease, track associated health markers, or identify dangerous fluid borne chemicals, using only small amounts of blood, urine, saliva, or other physical specimen. However, widespread adoption of this technology has been limited in part due to the cost and size of spectrometer equipment.

One of the more expensive components of a spectroscope can be the light source, which is typically a laser, LED, or broadband light source. In addition to component cost, light sources require substantial amounts of power to run, can be subject to drift in light intensity and spectral properties over time, and can be difficult to assemble or replace. Light sources are a particular problem for portable or disposable spectrometers, which require low power or low cost components for commercial adoption.

DETAILED DESCRIPTION

Embodiments are described in detail with reference to the drawings. Features and structures contained in attached drawings are schematic representations of embodiments of the present invention and are not drawn to scale; relative dimensions of the features and structures depicted are not accurate. In particular, for ease of explanation and illustration, even in the same drawings, some of the features or structures are exaggerated or magnified by one or more orders of magnitude as compared with other features of the drawings.

Figure 1:
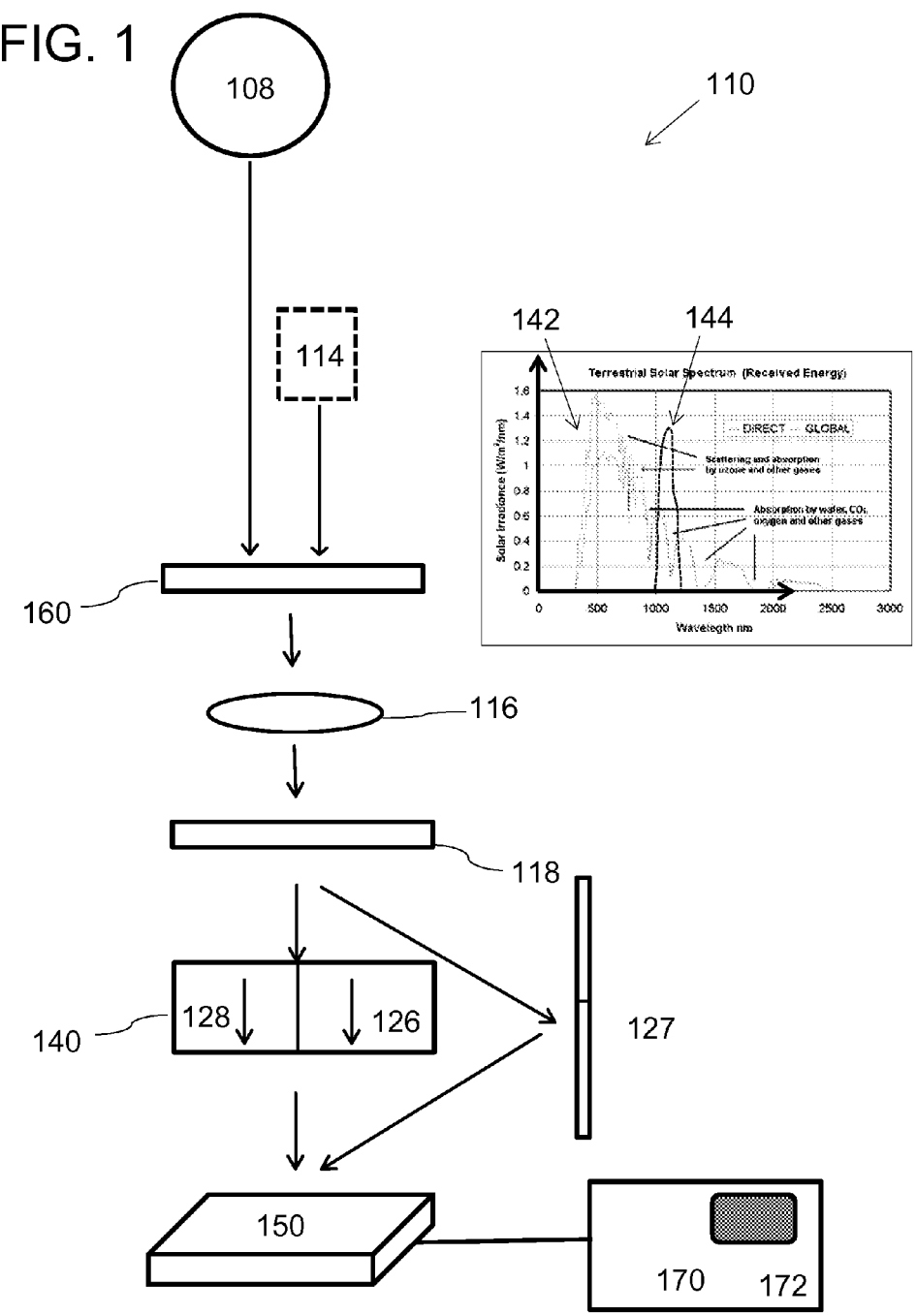
FIG. 1 is a view of a spectrometer embodiment.

FIG. 1 illustrates a spectrometer system 110 including an ambient light source 108, an optional aperture 160, an optional auxiliary light 114, collimation optics 116, and optional filter 118. Incoming light interacts with an analyte sample 128 and or control sample 126 held in a sample container 140 or present on a reflective surface 127, before being detected by a detector 150. The detector 150 is connected to processor 170 for system control, data analysis, and result output potentially using optional display 172. In disclosed embodiments, ambient light, which may be solar light, room light including incandescent bulbs, LED bulbs, fluorescent stip lights, compact fluorescent bulbs, coal or wood or other fires, or any other source of light which may typically be available to a user having a spectrum 142 is the light source, but selected wavelengths of light can be added to provide greater intensity at selected peaks (e.g. peak 144). Ambient light source 108 can include sunlight, some discharge lamps such as xenon or deuterium, incandescent lamps, halogen lamps, fluorescent lamps, or white LEDs. In some embodiments, a lamp with multiple line spectra such as a mercury arc lamp may be utilized.

In operation, spectrometer system 110 is activated by control electronics 170, ambient light is collimated, optionally filtered to provide selected spectra, which may be narrowband, wideband, or multi band, polarization or other desired optical properties, and caused to interact with samples. Spectroscopically detectable changes due to analyte presence can be measured with the detector and compared to null and or control samples 126 for qualitative or quantitative assessment of analyte presence.

In addition to ambient light, other optional auxiliary light source(s) 114 can be used to selectively intensify selected wavelengths or provide additional wavelengths not available in the ambient light source 108. Optional auxiliary light source(s) 114 may include monochromatic sources or virtually monochromatic sources such as diode lasers, dye lasers, tunable lasers, gas lasers, frequency doubled lasers, vertical cavity surface emitting lasers (VCSELs), or any other type of laser. In other embodiments, the light source can be near monochromatic, wherein a limited range of wavelengths from a spectrally broader source may be utilized. For example, a source such as a light emitting diode ("LED"), an organic light emitting diode (OLED), a quantum dot light emitting diode (QLED), a carbon nanotube LED, a filament lamp, a low pressure sodium lamp, some discharge lamps, or super luminescent diodes may be used.

Collimation optics 116 are generally required for improving directionality of ambient light sources. Use of a collimation element is also recommended for optional auxiliary light source(s) 114. Collimation optics 116 may comprise, at least in part, refraction elements, pinholes, or reflectors. In some embodiments, a collimator may at least in part comprise an aspheric or Fresnel lens or lens system. In some embodiments in which auxiliary laser light sources are employed, a laser collimator may also comprise a beam expander such as a 5× or 10× beam expander. In some embodiments, a self aligned spatial filter as described in a commonly owned, concurrently filed U.S. Application No. PCT/US2013/072929, entitled "Self-Aligned Spatial Filter", claiming the benefit of Provisional Application No. 61/784, 250, entitled "Self-Aligned Spatial Filter, filed Mar. 14, 2013, may be utilized to collimate the ambient and or auxiliary light source(s). The U.S. Application PCT/US2013/072929 is hereby incorporated by referenced in its entirety. As described in the U.S. application PCT/US2013/072929, the beam expander may be positioned in the optical path prior to the sample holder 140, or may be positioned after the sample holder 140.

For particular embodiments benefiting from a high intensity broadband source, sunlight can be used as the ambient light source. Sunlight is considered as a collimated ambient light source. However, reflection, scattering and absorption in the atmosphere, as well as the divergence and refraction of sunlight may result in sunlight not being a properly collimated broadband source. This is particularly when there is a significant amount of particulate material or water vapor such as clouds are present in the atmosphere in the area in which sunlight is being used as a source. As a result, the sunlight is typically collimated before transmission toward the optional filter 118 and analyte sample 128 and or control sample 126. Collimation may also be needed for effective filtering of the source, as dielectric filters can be angle dependent. As the amount of sunlight collected may vary significantly under different conditions, it may be desirable to check the amount of light which may be delivered to a device sensor. The system may determine whether sufficient light, or excessive light is being delivered. The system may manually or automatically adjust the exposure time and or portion of the dynamic range of the device sensor such that the amount of light and signal level is neither insufficient nor excessive. If the system is unable to adjust the exposure time and or portion of the dynamic range of the device sensor such that the amount of light is neither insufficient nor excessive after changing the exposure time and or portion of the dynamic range of the device sensor over the maximum range of adjustment, the system may adjust optional aperture 160, or alert the user that a manual aperture change is required, or that insufficient or excessive light is present. In alternative embodiment, the system may adjust the optional aperture 160 prior to adjusting the exposure time, or may alter both together, either simultaneously, alternatingly between adjusting the exposure and adjusting the aperture, or in any manner which provides for an appropriate adjustment of exposure and aperture such that the amount of light and signal level is neither insufficient nor excessive.

Collimation of sunlight may be achieved by a two or more aperture system. The divergence of the nominally collimated sunlight can be set by the aperture size and spacing. The apertures may be adjustable irises, or may be pinholes, or may be pinholes which may be manually or automatically interchanged. In an additional embodiment, the apertures may be provided by the use of fixed and or adjustable slits, or a combination of slits and irises or pinholes and slits. In other embodiments, a collimator may comprise a light pipe or fiber optic, wherein light may be coupled or focused into the light pipe or fiber optic, and light emerging from the opposite end of said light pipe ore fiber optic may be focused such that the emerging light is collimated. If a light pipe is utilized, a further advantage of said light pipe is that the shape of the emerging beam is the shape of the light pipe, which may be made to align well with the area which is to be illuminated.

In some embodiments, the optical path may be separated and different filters may be used for the different light paths. The different light paths may interact with the analyte sample 128 and any plasmonic elements associated thereto at different input angles.

The optional filter 118 receives collimated light and acts to improve light quality, provide light of desired characteristics (e.g polarized light) and/or allow for selection a bandpass wavelength or set of bandpasses. Various types of filters may be useful for these purposes, including colored glass filters made of an appropriate thickness so as to provide a desired optical filtering level. In an alternative embodiment, a colored filter may be molded as a lens, so that said colored filter may perform both the function of a filter and the function of a lens with a single part. In alternative embodiments, a color filter may be a multilayer dielectric or a rugate filter. Filters may be bandpass, longpass, shortpass, multipass, tunable bandpass, longpass beamsplitter, shortpass beamsplitter, notch beamsplitter, or a multiedge beamsplitter. A dielectric filter may be configured as a transmission filter, as a curved or flat mirror filter, or as a polarizing transmission filter. A dielectric filter may be made with soft coatings, hard coatings or a combination thereof. Color filters may be made of a combination of different technologies, such as a combination of colored glass and dielectric filters, dielectric filters and rugate filters, or any other combination of filter types. Color filters may be changed utilizing filter wheels or sliders, which may be manual, or may be automated. Light can also be filtered to be circularly or elliptically polarized, linearly polarized with s or p polarization components or a combination thereof, non-polarized, or selectively polarizable, wherein the polarization angle and or phase of linearly, circularly or elliptically polarized light may be adjusted.

For modulation of the incident light or other purposes, unpolarized light from the light source may be polarized by any of a variety of different types of polarizers, such as a Glan-laser polarizer, a Glan-Tayler polarizer, a Glan-Thompson polarizer, a Lyot polarizer, a Wallaston polarizer, a Rutile polarizer, a line plate polarizer, a polarizing film, a wire grid, a holographic wire grid or any other type of fixed polarizer may be utilized. In some embodiments, the polarization filter or polarization element(s) may be in a part of the optical path wherein the beam may be a collimated beam. In other embodiments, the polarization filter or polarization element may be utilized in a part of the optical path wherein the beam may have a divergence or convergence such that variation in the polarization of the resulting beam does not interfere with the desired interaction with the diffraction element. A quarter wave plate or a quarter wave or rhomb retarder may be utilized to convert linearly polarized light into circularly polarized light. A half, three quarter or full wave nematic liquid crystal variable retarder may be utilized to vary the phase retardation. The liquid crystal variable retarder may be temperature controlled. Continuous phase retardation may be effected using a Solei-Babinet compensator or similar device, which may be manually adjusted, or may utilize a motorized actuator.

In some embodiments, multiple types of polarization may be utilized. In some embodiments, different sources may have different wavelengths, different polarizations, different polarization phase angles with respect to each other, or different magnitudes with respect to each other or combinations of any of the above. In some embodiments, polarization may be changed, for example the polarization of a single source may be switched from being linearly polarized to being circularly polarized, or may be switched from having s linear polarization to having p linear polarization.

After collimated ambient light and any optional auxiliary light has passed through the optional filter 118, it may be directed to either or both of the sample container 140 and reflective surface 127. The sample container 140 can include analyte containing control 126 and/or analyte sample 128 with light directed therethrough interacting with analytes and being spectroscopically detectable. The sample container 140 may be formed using any solid material that can hold the gas or liquid therein and that is transparent to the incoming light. For example, it may be made from polymer by molding and/or machining. Laser machining, mechanical drilling, powder blasting, waterjet cutting, injection molding, hot embossing, and/or polymer casting, etc., can be used. Other appropriate materials for the container include silica, quartz, and silicon, for example. Micromachining techniques or other techniques can be used to form the side walls and the top surface of the container first, and then the machined container structure can be bonded on the metal layer with an appropriate adhesive to complete the construction of the container. In certain embodiments, the container can be made inexpensively to allow for disposable and/or single use.

A non-exhaustive list of analytes to be detected in a sample includes naturally-occurring or synthetic molecules including carbohydrates, proteins, lipids, oligonucleotides, nucleic acids, any organic polymeric materials, inorganic materials, including but not limited to salts, metals, or metal complexes. Exemplary analytes include celluloses, aqueous solutions, deionized water, blood, physiological buffer or other buffers which may also include salts, cerebrospinal fluid, urine, saliva, water, organic solvents, or combinations thereof.

After light interacts with the sample, it may be detected by a sensor. In certain embodiments the sensor is a two dimensional sensor. The detector 150 can include, but is not limited to, conventional pixel or focal plane array (FPA) devices, including a front or back illuminated charge-coupled device (CCD), a photon penetration depth dependent CCD, a photo-diode array (PDA), an avalanche photodiode (APD) array, a PMT array, or a front or back illuminated complementary metal-oxide semiconductor (CMOS) detector. For low cost embodiments, consumer CMOS detectors can be used with suitable modifications. Alternatively, a CCD chip can be used for applications requiring greater count accuracy, quantum yield, or binning flexibility. The sensor may be cooled or temperature stabilized. The sensor may be a monolithic sensor, or may be a hybrid sensor with different sections of the sensor utilizing different materials (such as silicon, InGaAs, HgCdTe), such that the different sections may have different wavelength quantum efficiencies, or the sensor may be a sensor assembly wherein multiple sensor chips may be integrated into a single sensor, which may be effectuated utilizing a PCB or hybrid assembly. Monochrome detectors can be used, or alternatively, detectors with conventional Bayer filters or other custom absorption filters can be used. Other detectors are possible, including long wavelength bolometers or the like. In preferred embodiments, low cost computational electronics and software, optical control electronics, and a CMOS or CCD based camera chip may be used in the detector electronics subsystem.

Local display of status, results, and error messages or the like may be afforded by display 172. OLED, LCD, bistable displays (electronic paper or similar) or other conventional displays can be used. Optional input pad can be a keyboard, touch sensitive element (which may be integrated as part of the optional display, or similar to provide for user input. In certain embodiments, a wired or wireless connect subsystem can be used to connect to a user interaction device such as a smart phone (not shown), external or integrated data processing device and external or integrated data recordation device. Optionally, data and control signals can be received, generated, or transported between varieties of external data sources, including wireless networks or personal area networks, cellular networks, or internet or cloud mediated data sources. In addition, spectrometer system 110 may include a source of local data (e.g. a hard drive, flash memory, embedded DRAM, or other known data retention systems) that can allow for firmware or software updating, and allows for data storage or control by direct user input or user-specified preferences or protocols.

Disclosed embodiments permit manufacture of portable or handheld device. Such a portable system can be used as a mobile or wearable device to monitor personal health, for high resolution color monitoring for color input, display and output devices, or as an environmental monitoring sensor such as for water or air quality sensors. The spectrometer system may be of particular use for low resource settings such as a remote village, and can optionally be used to provide individuals with information relating to nutrition/liver panels, protein markers which indicate severity of trauma or disease, or even direct identification of infectious diseases. Other applications include long term, low cost monitoring of diabetics (particularly for non-glucose markers), individuals taking costly or concentration sensitive drugs (e.g. anti-clotting drugs such as warfarin), CD4 cytometry or other suitable biomedical applications. Still other uses can include industrial monitoring, including processes and/or equipment requiring non-invasive sensing of chemical compounds.

Figure 2:
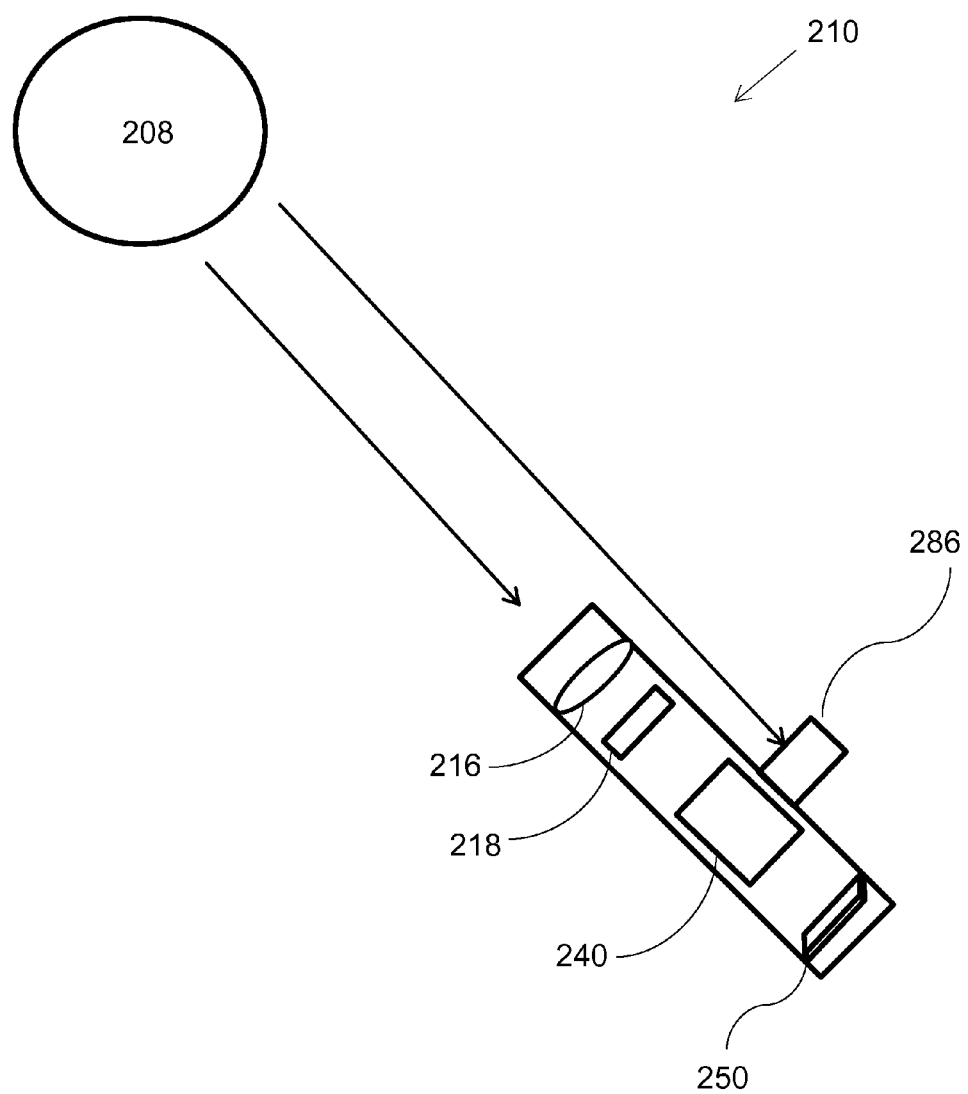
FIG. 2 is a view of a portable, hand holdable spectrometer pointable at an ambient light source such as the sun or an incandescent room light.

FIG. 2 is a view of a portable, hand holdable spectrometer device 210 pointable at an ambient light source such as the sun or an incandescent room light. The spectrometer of FIG. 2 includes an ambient light source 208 which may be the sun, collimation optics 216, an optional filter 218, a sample container 240, a detector 250, and an aiming device 286.

In some embodiments where a relatively short set of data is needed, a user may point the device towards the light source 208 (sun), and the system may alert the user when the set of data has been successfully taken. In some embodiments, it may be sufficient to simply wave the hand holdable spectrometer system 210 in the direction of the light source 208 (sun), and during the short period of time when collimation and insolation level are sufficient, data may be taken. In other embodiments, where solar light levels are lower and or when a longer period of time is needed to take data set, the user may need to more directly point the device towards the light source 208 (sun), so that the hand holdable spectrometer system 210 has sufficient time to take a desired data set. In some embodiments, the system may provide an audible or visible feedback to the user, for example changing pitch, frequency, or volume of a tone, or changing the intensity or size or color of a visual feedback element(s). The change in pitch frequency, or volume of a tone, or changing the intensity or size or color of a visual feedback element(s) may accompany an increase in alignment to the sun, allowing the user to better align the device such that proper collimation may be provided. The system may provide a definitive audible or visual notification to the user that a set of data has successfully been taken by for example changing pitch, frequency, or volume of a tone, or changing the intensity or size or color of a visual feedback element(s) to a pitch, frequency or volume of a tone not normally used, or may use a more an audible alert such as simulated bell sound or any other appropriately positive sound, wherein the sound may be selected by the user as to the type of sound, its duration and the decibel level of the sound, or the system may provide a visual alert to the user in the form of a text message, or a graphics pattern or video which may be of the user selected. In some embodiments a combination of sound and visual alert may be utilized.

In some embodiments, the user may visually align the hand holdable spectrometer system 210 towards the light source 208 using the aiming device 286. If the light source 208 is the sun, the aiming device may have a neutral density filter with appropriate optical density, such as about an optical density of 4.5 in the UV and visible spectrum and an optical density of about 2.5 in the near infra-red associated thereto so as to reduce the intensity level of the light source 208 (sun) and prevent eye damage. Similarly, the aiming device may have a neutral density filter with appropriate optical density as appropriate for use with other bright sources. Such an aiming device may be useful for cases when a longer exposure is needed, so that the user can visually provide optical feedback to insure proper alignment to the light source 208.

Figure 3:
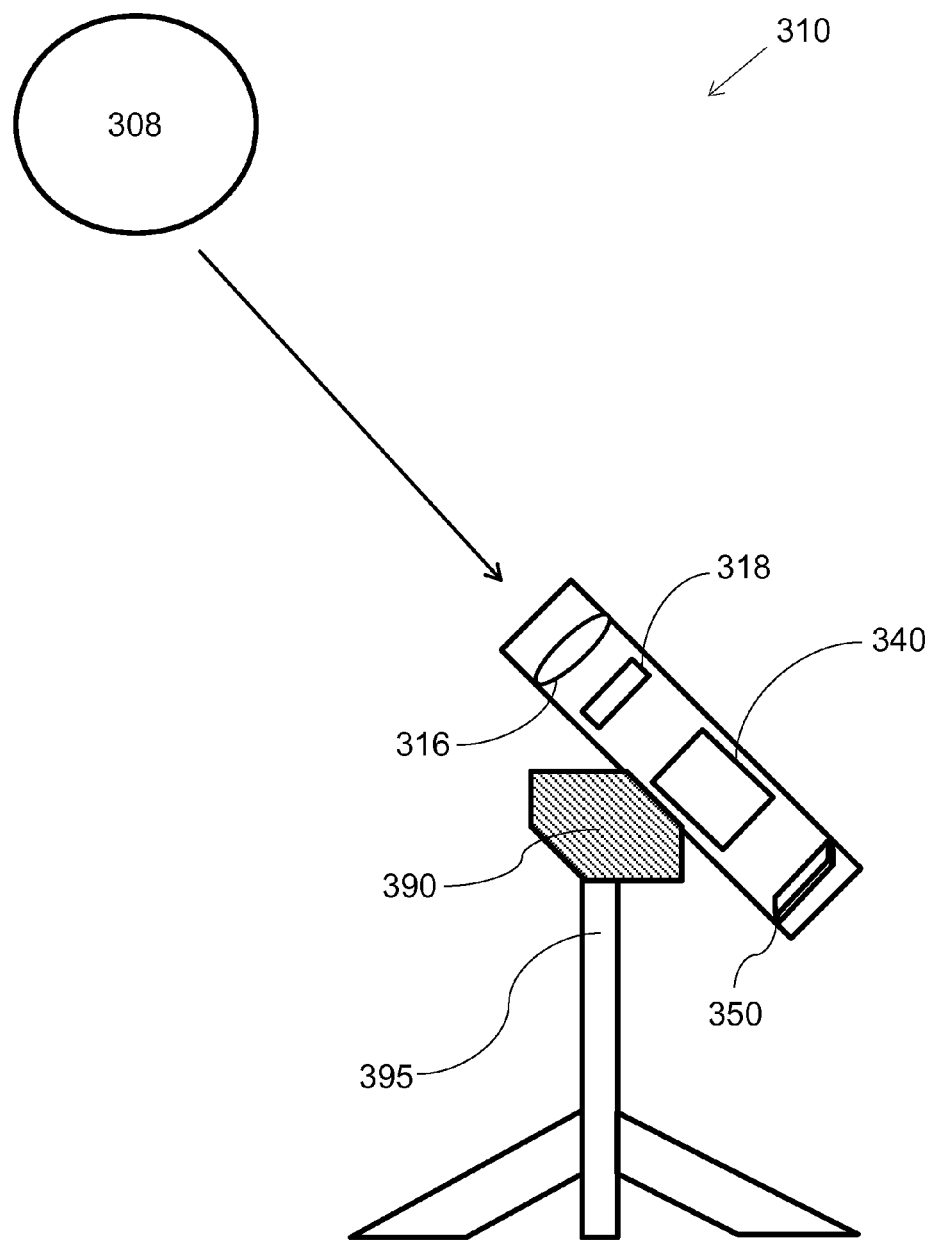
FIG. 3 is a view of a spectrometer with light tracking capabilities.

FIG. 3 is a view of a tracking spectrometer system 310 which may be manually or automatically pointable at an ambient light source 308 such as the sun. The spectrometer system 310 of FIG. 3 includes an ambient light source 308 which may be the sun, collimation optics 316, an optional filter 318, a sample container 340, a detector 350, a mount 390 and a supporting device 395.

Figure 4:
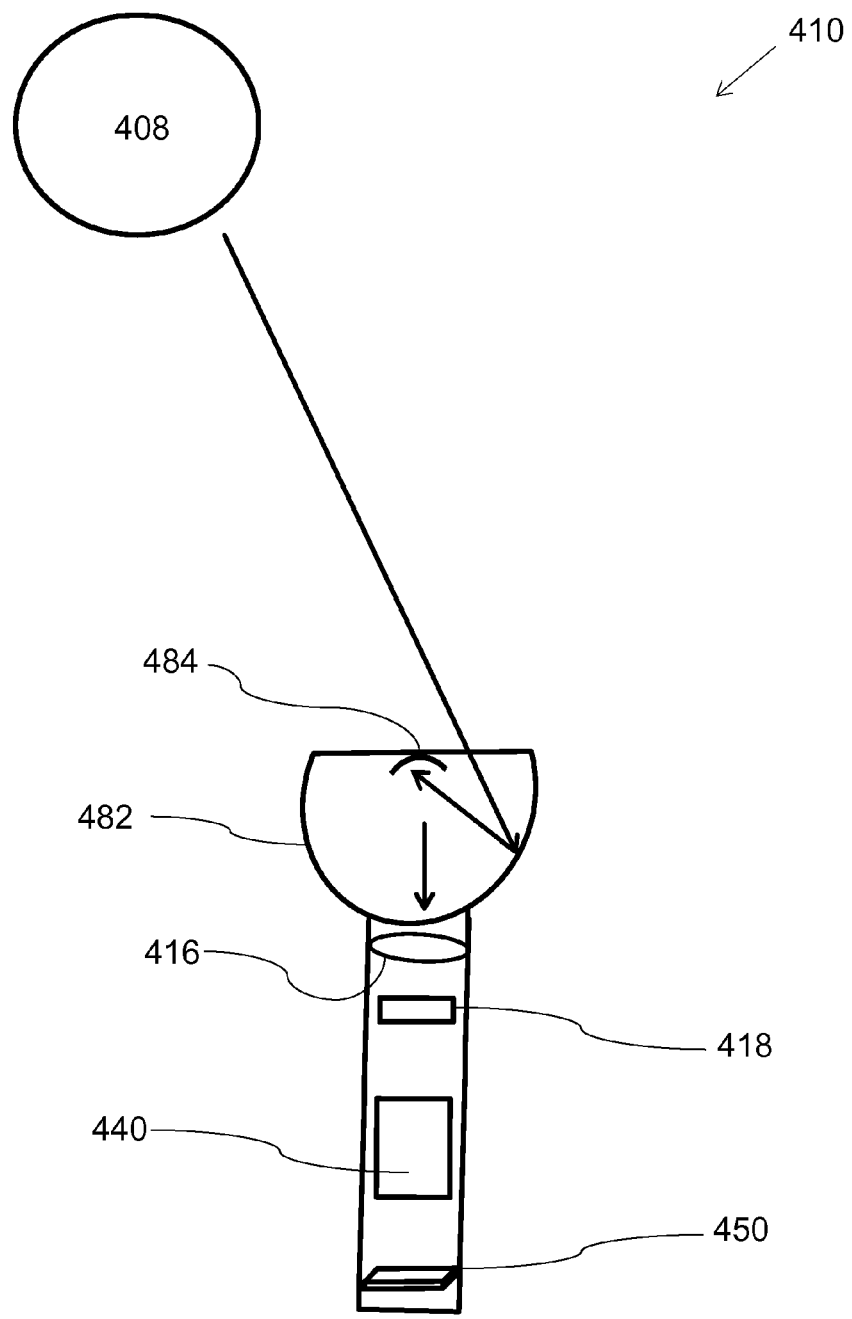
FIG. 4 is a view of a spectrometer with multidirectional ambient light input.

As seen in FIG. 3 in some embodiments, the spectroscopy device 310 may comprise a mount 390, and a supporting device, which may be a tripod, and may be integrated with the mount 390 to stabilize the spectrometer system 310 such that it may be properly aligned and held, pointing towards the light source 308 (sun). This may be particularly desirable under conditions wherein the sunlight may be dim, such as when the light source 308 (sun) has just risen or is about to set, or when conditions are quite cloudy. Said mount 390 may be a manual equatorial mount such as an Orion Min-EQ Equatorial Scope & Camera Mount or a star tracking mount such as a Vixen Polarie or Orion StarShoot Autoglide, particularly when a set of data is desired over a period of time sufficient that the sun may have moved relative to the device during the time over which said set of data may be taken. The adjustment which is provided by a motorized equatorial mount may be needed when the kinetics for a reaction which is being monitored are quite slow, or when a series of reactions are being monitored, while a manual equatorial mount may be useful when a series of measurements are being made FIG. 4 is a view of a spectrometer system 410 capable of multidirectionally capturing ambient light source such as the sun or incandescent room lights. The spectrometer system 410 of FIG. 4 includes an ambient light source 408 which may be the sun, collimation optics 416, an optional filter 418, a sample container 440, a detector 450, a primary reflector 482, and a retro-reflector 484.

Both the primary reflector 482 and the retro-reflector 484 may be elliptical, parabolic, hyperbolic, spherical, segmented, or may be of any other appropriate function or shape suited for capturing and collimating light input to the spectrometer system 410. The primary reflector 482 and retro-reflector may be linearly or axially symmetrical with respect to the optical axis entering the spectrometer system 410, and may be made of a material or may be coated with a material or set of materials which preferentially reflects wavelengths of interest for the system. In some embodiments, the primary reflector 482 and or retro-reflector 484 may be removed and replaced with another primary reflector 482 and or retro-reflector 484 which may preferentially reflect a different set of wavelengths.

The primary reflector 482 and the retro-reflector 484 may be formed of a specular clear anodize coating for aluminum such as Alzak® or other similar coatings, or may be a clear diffuse coating, or may be a highly reflective coating such as those used for integrating spheres such as barium sulfate or a packed or sintered PTFE coating, or may be a solar reflective paint to collect infrared radiation such as those used for "cool roofs", or may be made with a dielectric coating.

Figure 5:
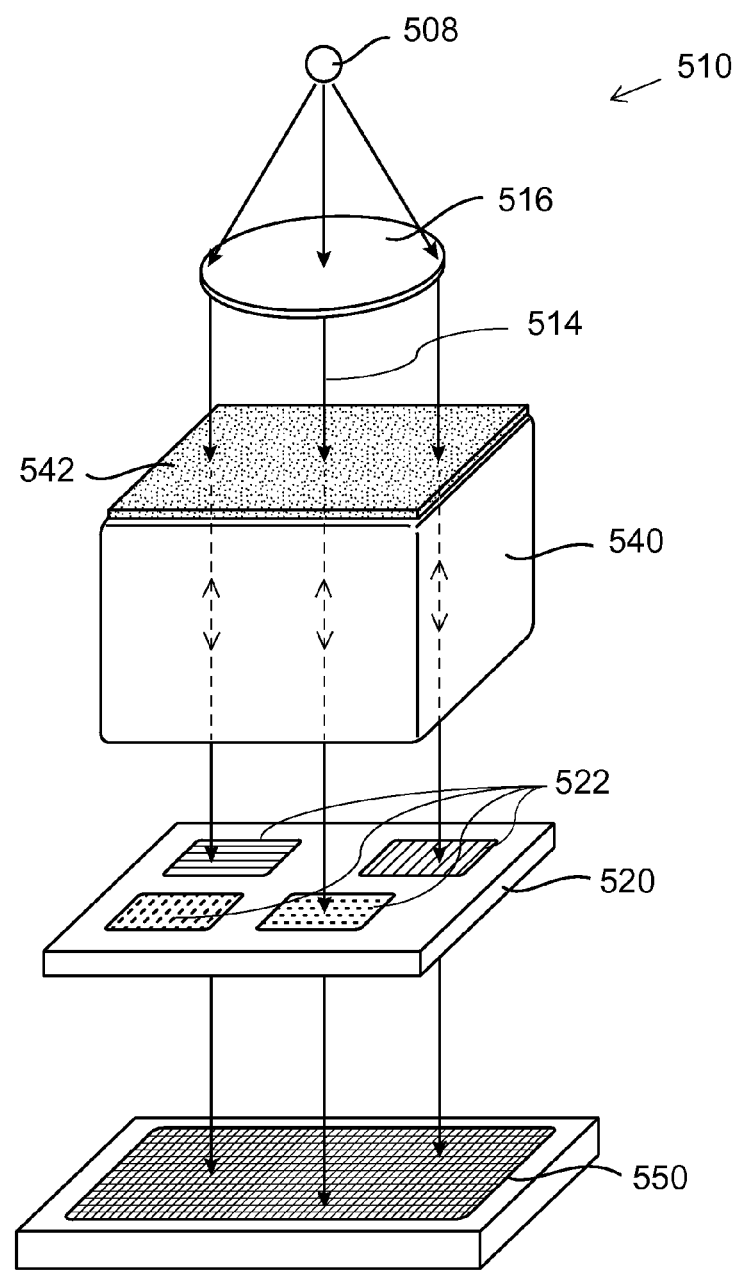
FIG. 5 is a view of an ambient light absorption spectrometer that includes plasmonic filters.

FIG. 5 illustrates a spectrometer system containing a light source directed into a sample containing sample holder 540, where light passing through the sample holder 540 may interact with plasmonic filters and the transmitted light intensity may be measured by a detector. As seen in FIG. 5, a compact and low cost spectrometer system 510 incorporating surface plasmon filter set 520 is illustrated. The surface plasmon filter set 520 supports one or more patches 522, with each patch 522 acting to filter light based on various properties, including wavelength or polarization angles. As will be appreciated, each patch 522 may include a number of plasmonic filters in an array.

In spectrometer system 510, light source 508 emits light 514 that is collimated by collimation optics 516, with light 514 directed to pass through sample holder 540. Sample holder 540 has at least one partially mirrored side 542. Sample holder 540 may contain one or more internal chambers capable of holding fluid samples. In this embodiment, the combination of mirrored side 542 and partially reflective plasmonic filter set 520 causes some percentage of light to be reflected back through sample holder 540, increasing the effective path length of light passing through the fluid. Light that passes through sample holder 540 may be modified by surface plasmon filter set 520, with each patch 522 selectively eliminating, enhancing, or otherwise modifying wavelength or intensity of selected light wavelengths during transmission. Patterned and filtered light may be detected by one or more addressed pixels on detector 550, with the pixels associated with a portion of a transmission pattern and light intensity from that portion being measured. Such measured changes in light intensity can be used to monitor the presence, absence, or absolute or relative concentration of analyte(s), or a change in concentration due to diffusion, flow, or kinetics of a reaction of analyte(s) diffusing into, held, bound, in or associated with the sample holder.

Collimating optics 516 can include a spherical lens, an aspheric lens, graded index (GRIN) lenses, light wave guides, mirrors or combinations thereof. In operation, collimating optics 516 generates a collimated beam of light 514. The focal length of collimating optics 516 may be selected based on the properties of the optical wave emitted by light source 508 to achieve the required incident light beam 514. Typically, a divergence or convergence angle of less than 1.0 degrees may be desired, but depending on the application and constraints of the optical system, larger divergence or convergence angles can be tolerated as needed for the desired effective finesse and transmission of the sample holder. In some embodiments, a beam splitter or several beam splitters may be utilized to separate different input light wavelengths, which may thence be utilized in different areas or regions. In a further embodiment, a grating or prism with slits may be utilized, with optional band pass or high or low pass filters to select different input light wavelengths which may be utilized in different areas or regions. In a further embodiment, the grating or prism may be manually or automatically adjustable, and a manually or automatically adjustable slit may be provided such that a wavelength and bandpass may be manually or automatically adjusted. In some embodiments, selected wavelengths and band passes may be utilized as part of an automated protocol. In yet further embodiments, a continuous scan over a range of wavelengths may be automatically performed, permitting the generation of a continuous data set of absorption as correlated with time.

Optionally, collimated light can be passed through an optical pattern generator to convert input light into output light having a preselected spatial layout and intensity pattern. This pattern may be created using diffraction, refraction, reflection, and/or other mechanisms, or a combination thereof. The optical pattern generator can include diffractive optical elements containing a glass, plastic, and/or fused silica chip designed and patterned by holography, photolithography, interference lithography, nanoimprint lithography, scribing, molding, and/or other methods to create a predefined illumination pattern from incident light. The optical pattern generator also may employ non-diffractive optics. For example, the generator could employ a lens array that focuses a large collimated beam. Alternatively, or in addition, refractive or reflective optical elements, such as a lens or beam splitter, can be used. The collimated beam from the collimator can be expanded and directed into a lenslet array that would focus the separated light onto multiple sample sites. A combination of refractive and diffractive optical elements may be utilized, for example, utilizing lenslets to focus light to different sample holders or to different regions or patches within a sample holder, while a diffractive optical element or a set of diffractive optical elements associated directly with each sample holder, regions within a sample holder or patch may generate a more localized illumination pattern associated with each sample holder, regions within a sample holder or patch, generating spots associated with regions or patches. The localized illumination pattern may be closely aligned with said regions or patches. In a further embodiment, multiple diffractive elements may be utilized wherein one diffractive element may be utilized to produce spots of uniform intensity associated with each sample holder or patch, and a second diffractive element or set of diffractive elements may be utilized to produce spots of light associated with each region or patch.

The optical pattern generator may be also be used to generate any desired pattern of light, including one-dimensional or two-dimensional patterns (or arrays) and periodic or aperiodic patterns. For example, a diffractive chip or similar optical pattern generator may be used to create any regularly shaped beam. For example, in applications requiring multiple sample holders, the pattern may be an array of substantially equally spaced substantially equally intense spots positioned to correspond to the spacing of the sample holders. Alternatively, the arrays could be positioned so that only specific regions within the same sample holder are addressed, or an array of light spots may be configured and positioned so that a number of specific regions may be illuminated on several sample holders. The spacings and diameter of the spots may be uniform on all sample holders and within all sample holders, or may vary between different sample holders, and within a single sample holder, or may vary both between and within sample holders. In some embodiments, the spacings within a single patch may be uniform, but may vary from patch to patch.

In some embodiments, wherein different sample holders or different sections of a sample holder associated with detectors which have different sensitivities and or different dynamic ranges, the intensity of the different spots may be adjusted to correspond with the different sensitivities and or dynamic ranges.

In some embodiments, uniform illumination across individual samples rather than across the entire illumination pattern may be desired, particularly with very large area arrays. However, uniform illumination across the entire pattern may be unnecessary for many assays, particularly assays such as kinetic and cellular assays that involve reading the samples before start of the kinetic or cellular assay, since the pre-start measurement may act as a reference for the post-start measurement.

As shown in FIG. 5, sampler holder 540 can be made of glass or transparent plastic material. A sample holder can be designed for single use analysis and disposal of a sample, or can be designed to allow multiple uses. Multiple internal sample holder chambers may be preferred when both control(s) and samples need to be compared. As will be appreciated, sample holder designs supporting multiple use applications can provide for washing and sterilization, or alternatively, can involve multiple single use chambers individually disposed in the sample holder 540, with separate sample or control fill inputs. In certain embodiments, the sample holder 540 can be separately filled outside the spectrometer system 510, and later inserted into the spectrometer system 510 for analysis, while in other embodiments one or more input and output ports can be integrally formed to allow fill or flushing of the sample holder while it is in an analysis position within the spectrometer system 510. The sample holder 540 can have a single or multiple flow channels, typically consisting of an input channel(s) and an output channel(s), along with suitable valving or fluid control mechanisms.

The sample holder 540 may function both as a fluid reservoir and an optical cavity. Without excluding other geometries, the sample holder 540 chamber will typically be cylindrical or conical in shape, and have a top surface capable of facing a light source and a bottom surface facing an image sensor(s). The top side of the sample holder 540 facing the light source 508 is generally transparent so as to admit incident light. In certain embodiments, the sample holder 540 can be partially or completely coated or attached to light filters or absorbers to reduce or enhance transparency at some or all wavelengths. In some embodiments, at least one of the internal face of the top side of the sample holder 540 (contacting or near the sample holder cavity) and the exterior face of the top side of the sample holder 540 (not contacting, and away from the sample holder cavity) is at least partially reflective to incident light and therefore forms one facet of an optical cavity. This facet will typically be coated with a thin film optical coating to engineer a desired optical response. Other coatings or inserts into the sample holder 540 can be used to isolate chambers or redirect light, including opaque walls or sidewalls that reduce optical crosstalk, light absorbing or reflecting coatings, or the like. In effect, using sample holder supported (or adjacently positioned) films or structures forms a partially mirrored optical cavity permitting light to travel multiple times between top and bottom of sample holder, effectively increasing the sample path length, wavelength dependent absorption, and or improved probability of interacting with related detector(s).

In some embodiments, selected sections of a sample holder may be utilized as control sections. In some embodiments, control sections may not have any target molecules or may be associated with reference samples of known composition and effect, and thus may be utilized to normalize variations in the output of the light source, absorbance of the fluid under observation, temperature, pressure of the input fluid, variations in the size, reflectivity and optical transmission of a consumable at different wavelengths. In other embodiments, one or more reference samples of known composition and effect and or calibration standards may be provided, either separately from or included with a sample, allowing further normalizations, including compensating for sensitivity, variations in input concentration, and variations in wavelength sensitivity.

In addition to modification of optical properties, chemical and fluid flow properties of the sample holder may be modified or controlled by coatings, inserts, gettering elements, microchambers, pore containing elements, filters, or partially permeable barriers. This may include hydrophilic or hydrophobic coatings or structures to improve or reduce fluid flow properties. In other embodiments, chemically reactive patches or gettering agents can be used to bind, absorb, or adsorb contaminating or undesired sample components such as proteins, molecules, or the like. In further embodiments, a surface treatment, surface modification or surface coating such as polyethylene glycol (PEG) may be utilized so as to minimize nonspecific binding. In still other embodiments, chemical functionalization can be used to localize analyte, or chemically reactive coatings, catalysts, structures, nanochambers, or the like can be provided so that the sample holder supports a desired reaction.

To quantify biological and chemical events or to identify a compound, a sample with a particular analyte may be held in the sample holder. Samples can be derived from materials of biological origin, such as tissue samples, blood, sputum, epidermal scrapings, etc., environmental materials such as soil, water, or air samples. A non-exhaustive list of analytes to be detected in a sample includes materials in solid, liquid or gaseous states, and may be comprised of naturally-occurring or synthetic molecules including carbohydrates, proteins, lipids, oligonucleotides, nucleic acids, any organic polymeric materials, inorganic materials, including but not limited to salts, metals, or metal complexes. Liquid solutions include those containing an aqueous, organic or other primary components, gels, gases, and emulsions. Exemplary solutions include celluloses, aqueous solutions, deionized water, blood, physiological buffer, cerebrospinal fluid, urine, saliva, water, and organic solvents.

Positioned below the sample holder may be one or more optical filters, contacting or in close proximity to the sample holder. Generally, an optical filter may be fabricated so that broadband light may be differentially absorbed or reflected, with transmitted light having a significantly different spectrum than the incident light. One common way of manufacturing color filters is to deposit two or more dielectric materials having different refractive indices on a transparent substrate such as glass. Typically, an interference optical filter is obtained if two or more materials having different refractive indices are stacked in several layers having various thicknesses on a glass substrate, wherein thicknesses of a quarter wavelength of the wavelength of interest are frequently utilized. An optical filter fabricated in such a manner can have a desired band characteristic and transmittance. However, close to atomic layer deposition control may be required for best results, many desired bandwidths may be difficult to manufacture, and such interference optical filters are angle dependent.

An alternative approach to generating an optical filter utilizes color filter glass or color photoresists as typically utilized in an RGB camera. Some filters may utilize a combination of interference filters and absorptive glass filters, particularly to provide lower angle sensitivity.

In order to make low cost and improved color filters, use of structurally patterned color filter layers is contemplated. Structural color filters are distinct in that they consist of a single layer that has lateral dielectric contrast, wherein said dielectric contrast may contrast the dielectric constants of different dielectrics, or may contrast the dielectric constants of one or more dielectrics and the dielectric constants of one or more metals, as opposed to the aforementioned interference optical filters which are structured in the out-of-plane direction. Structural color filters are relatively simple and affordable to fabricate; although they do require patterning and deposition or removal steps, low cost and widely available patterning technologies such as lithography can be used, as well as more advanced patterning techniques as nano-imprinting or self-assembly. Typically, a structural color filter can be formed by selective etching or deposition of a single layer deposited by various techniques including sputtering, evaporative coating or other physical vapor deposition techniques, chemical vapor deposition, electroplating or other conventional coating technologies. Examples of structural color filter layers include photonic crystals and plasmonic color filters.

Plasmonic color filters, specifically, consist of patterned layers in which one or more of the constituent materials may be a plasmonic material. When light is incident to a plasmonic material, electrons near the surface of the metal oscillate in response to the incident electric field, forming a surface plasmon or surface plasmon polariton excitation. The spectral properties of light transmitted by a plasmonic color filter can be significantly modified from that of the incident light and may be controlled by selecting composition, microstructure, thickness, and patterning of the plasmonic material and the surrounding dielectric environment. The composition of the plasmonic material may be selected to accommodate the desired spectrum of light to be transmitted, for example gold may be selected to transmit visible and near-infrared light while aluminum or silver may be selected to transmit near-ultraviolet light. In some embodiments, all plasmonic color filters may be fabricated using the same plasmonic material composition, thickness, and microstructure while in other embodiments, multiple plasmonic material compositions, thicknesses, and microstructures may be incorporated within or amongst a set of plasmonic color filters.

The plasmonic color filter patterns may be formed by any suitable method. For example, a masking layer may be formed and structures may be defined using photolithography, e-beam lithography, imprint lithography, or focused ion beam milling. The structures created in the masking layer can subsequently be used to create a pattern in the underlying plasmonic material by chemical or physical etching, lift-off methods, or selective growth methods. Alternatively, the patterns may be formed in the plasmonic material without a masking layer by the selective deposition of structures on a prepared substrate or by forming a seed layer on the film and patterning the layer into the structures by electroplating, electroless plating, or any combination of disclosed methods. In other embodiments, a plasmonic material may be directly patterned using focused ion beam milling. In some embodiments, an adhesion layer such as $TiO_2$, $Cr_2O_3$, Ti, Pt, Ni or Cr, may be utilized to better adhere a metal film or films, wherein the thickness may be less than 25 nm. In other embodiments, the metal film or films may be directly adhered to the substrate.

In certain embodiments, auxiliary filters can be used above or below the sample holder, and above or below the structural color filter. Conventional dielectric filters, polarizing filters, absorption filters, or combinations thereof can be used, as well as more sophisticated active filters. In one embodiment, the auxiliary filter comprises a device or mechanism capable of selecting the wavelength composition (or spectrum) of light admitted to the detector. Such emission spectral filters include absorption filters, interference filters, liquid crystal tunable filters, acousto-optic tunable filters, electro-optic tunable filters, gratings, monochromators, and/or prisms, among others. One or more filters having suitable spectral characteristics (e.g., bandpass and band center) may be housed in one or more filter selectors such as a filter wheel or filter slider so that the wavelength composition of the excitation admitted into the sample holder, or emission light admitted to the detector may be changed by rotating or sliding or otherwise placing a preselected filter into the optical path. Any of the filters or filter selectors may be placed under computer control to automate filter selection, which may be further coordinated with excitation wavelength selection. Alternatively, a motorized grating or prism may be utilized with an adjustable slit to select a band center and bandpass respectively.

Emission spectral filters may be used to transmit emission light and block excitation light in photoluminescence applications. Specifically, emission spectral filters with appropriate cutoff wavelengths can separate emitted light from incident (excitation or illumination) light due to differences in wavelength. For example, in conventional photoluminescence assays, the detected (emission) light is of longer wavelength than the corresponding illumination (excitation) light. In contrast, in multiphoton photoluminescence assays (and in anti-Stokes Raman scattering), the detected light is of shorter wavelength than the corresponding illumination light. In the absence of an emission filter, stray excitation light created, for example, by scattering and/or reflection may be detected and misidentified as photoluminescence, decreasing the signal-to-background ratio.

After light passes through the collimator, the sample holder, and various structural color filters or auxiliary filters, it may be detected by a two dimensional sensor. The detector 550 can include, but is not limited to, conventional pixel or focal plane array (FPA) devices, including a front or back illuminated charge-coupled device (CCD), a photon penetration depth dependent CCD, a photo-diode array (PDA), an avalanche photodiode (APD) array, a PMT array, or a front or back illuminated complementary metal-oxide semiconductor (CMOS) detector. For low cost embodiments, consumer CMOS detectors can be used with suitable modifications. Preferably, such detectors may have a pixel count in excess of the number of plasmonic color filters. Alternatively, a CCD chip can be used for applications requiring greater count accuracy, quantum yield, or binning flexibility. The sensor may be cooled or temperature stabilized. The sensor may be a monolithic sensor, or may be a hybrid sensor with different sections of the sensor utilizing different materials (such as silicon, InGaAs, HgCdTe), such that the different sections may have different wavelength quantum efficiencies, or the sensor may be a sensor assembly wherein multiple sensor chips may be integrated into a single sensor, which may be effectuated utilizing a PCB or hybrid assembly. Monochrome detectors can be used, or alternatively, detectors with conventional Bayer filters or other custom absorption filters can be used. Other detectors are possible, including long wavelength bolometers or the like.

An optional undercoat or "spacer" layer(s) may also be utilized across the whole surface of the sensor. Such a layer can provide a electronic isolation functionality, function as an adhesion layer, support planarization of the sensor (if it is substantially non-uniform), provide a protective barrier layer that protects, for example, the sensor from unwanted conductive metal diffusion. In certain embodiments, the spacer can include a long wave pass filter to select the correct diffractive order, or to reject excitation light in a fluorescent device. In still other embodiments, the spacer layer can contain a phosphor including lanthanides, or other rare earth elements or transition metals, or lanthanide complexes such as chelate stabilized lanthanides or other rare earth complexes or transition metal complexes, or quantum dots to act as an wavelength up-conversion or down-conversion layer. This can allow an improved match between the wavelength of the spectroscopic signal and the sensitivity band of the sensor. In some embodiments, a wavelength up-conversion or down-conversion layer may be positioned in the immediate vicinity of a plasmonic color filter such that enhanced electromagnetic field intensity can be used to improve the efficiency of nonlinear conversion processes. For example, a lanthanide-based phosphor layer may be positioned within 500 nm of the plasmonic color filter to provide near-field coupling between surface excitations such as surface plasmon polaritons and the phosphor layer. The phosphor layer may be positioned more than 10 nm away from the plasmonic color filter to suppress quenching of luminescence via so-called "lossy surface waves". In some embodiments, a spacer can separate a sensor from a sample holder and may provide chemical and/or mechanical protection. An overcoat layer may additionally improve optical, thermal or electronic matching between a sensor and a sample holder, and may provide antireflection, electrical or thermal impedance matching.

The transmitted light from each plasmonic patch 522 can be addressed to one or more pixels on the focal plane array. Typically, pixels on the sensor may be correlated, associated with, physically aligned with, or matched to specific pattern patches 522 of plasmonic color filter(s). In one embodiment, pixels on a sensor may be associated with transmitted light selectively using an algorithm incorporating calibration measurements performed after the assembly of the spectroscopy system and/or after the coordination of a sample to be examined within the system. For example, a filter can be used to identify pixels associated with transmitted light on the basis of an intensity threshold with a geometric shape invariant related to the geometry of specific pattern patches. One pixel can be matched to one filter pattern, or alternatively, multiple pixels can be illuminated by one patch.

A spectral measurement of the optical extinction of the sample holder 540 contents may be correlated to the intensity signals from spatially distinct pixels. Suitable linear algebra calculations can associate observed intensity to the signal intensity via a filter transfer function matrix, which may further include data for the dark current of the sensor, background signal levels without an excitation being provided, and baseline signal levels when there is no sample present. Multiple independent "micro spectrometers" can thus be formed, with each micro spectrometer associated with separate chambers including control and sample chambers, or multiple independent micro spectrometers may be associated with different regions within a single chamber, wherein the different regions may have different associated reagents. In still other embodiments the sample holder can support structures or coatings that provide a gradient of diffusion, such that the different regions may measure different reagents in a sample.

Figure 6A:
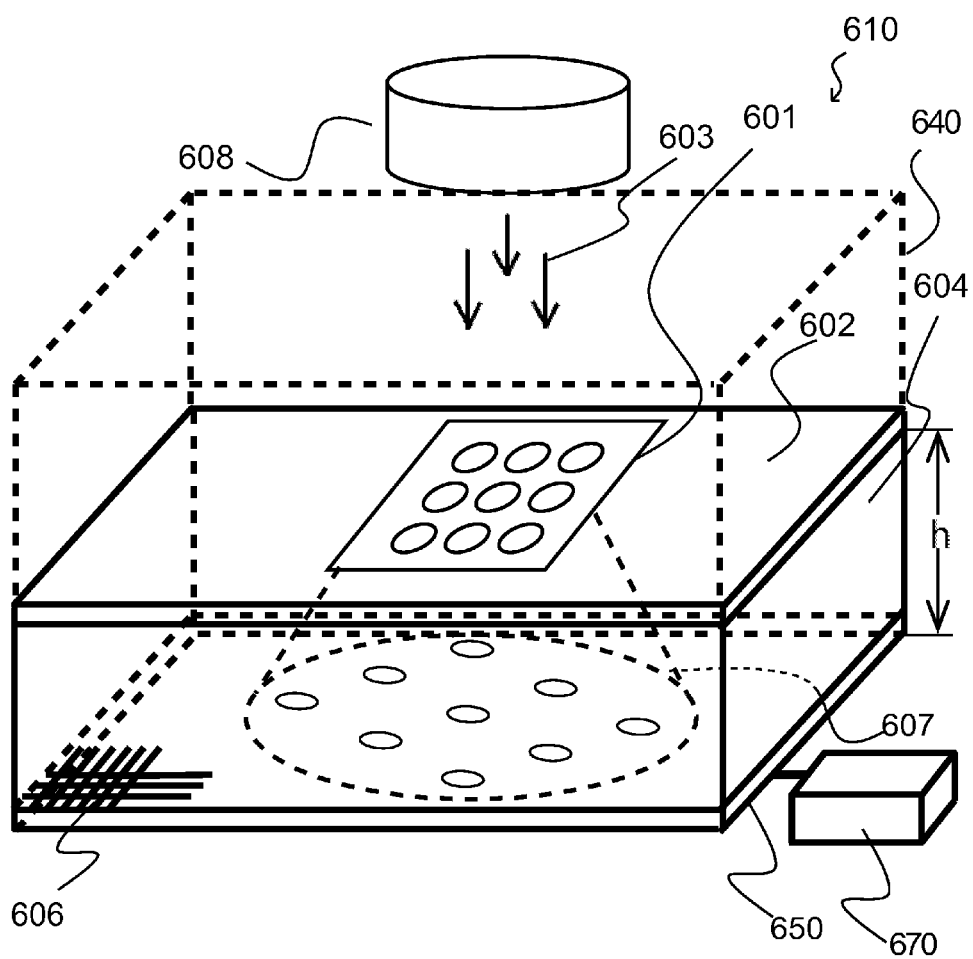
FIGS. 6A and 6B are a view of an ambient light projected diffraction spectrometer that includes plasmonic diffraction elements.
Figure 6B:
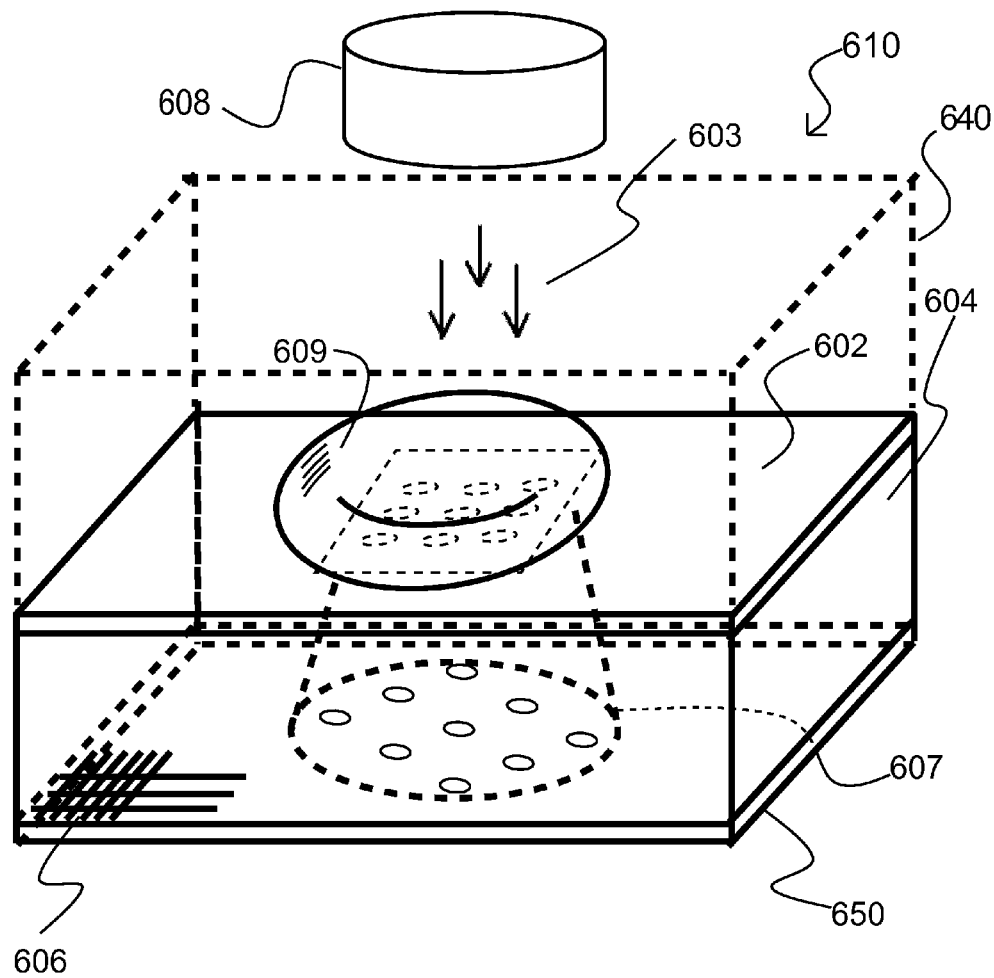

FIG. 6A schematically illustrates a compact, low-cost projected diffraction spectroscopy system 610 according to one embodiment. The spectroscopy system 610 is designed to detect the presence of specific chemical analytes (target substances) by monitoring changes in refractive index caused by the presence of the analyte. FIG. 6A shows a configuration of the spectroscopy system 610 when target substance 609 is absent, and FIG. 6B shows the same when the target substance 609 arrived at a detection site.

Referring to FIG. 6A, the spectroscopy system 610 includes: a light source 608 emitting substantially monochromatic light 603; a sample holder 640 capable of holding a solution that includes one or more types of target substances/analytes; a diffraction element 601 in a metal layer 602 that interacts with the light from the light source and projects a diffraction image 607 therebelow; a dielectric layer 604; and an image sensing detector 650 for detecting the diffraction pattern projected thereto. Processor 670 is provided to process signals from the image sensing detector 650.

The sample holder 640 can be formed in whole or in part of a material substantially transparent to the light 603 emitted from the light source 608 so that the light 603 interacts with the diffraction element 601 in the metal layer 602. Although the sample holder 640 has a structure adequate to contain the solution with the target substances therein, it is drawn by dotted lines to show structures underneath clearly.

The light source 608 includes ambient light (derived from sunlight, some discharge lamps such as xenon or deuterium, incandescent lamps, halogen lamps, fluorescent lamps, or white LEDs, or the like, and optional light emitting device (s), which can include but is not limited to a laser diode, a light emitting diode (LED) or a vertical cavity surface emitting laser (VCSEL). In addition, an optical filter and/or collimating optical system may be included in the light source 608. A polarizer or polarizing optical system may be included in the light source 608 or separately provided below the light source 608. The resulting direct or filtered light interacts with the diffraction element 601. The light source 608 preferably emits substantially monochromatic light with a certain degree of coherence. The degree of the coherence and the bandwidth of the emitted light should be such that the diffraction pattern projected onto the image sensor (which will be described in detail below) exhibits sufficient key features to be recognized by the image sensor for the diffraction element used. With an appropriately designed diffraction element and an image sensor having a sufficiently dense pixel array, a visible light semiconductor LED having a center wavelength with a bandwidth of a few tens of nanometers may be used as the light source 608 or as the light emitting device to be included in the light source 608 together with other optical components. A laser diode having a narrower bandwidth with higher coherence may also be used.

In this embodiment, the light 603 from the light source 608 is incident upon the sample holder 640 in a direction substantially normal to a plane defined by the diffraction element 601.

In this embodiment, the diffraction element 601 is structured to have one or more openings that are empty or filled with a dielectric in the metal layer 602 so that plasmon waves are generated upon receipt of the light from the light source 608. That is, the openings of the diffraction element 601 are the features that can generate or otherwise launch plasmon waves. The plasmon waves are sensitive to the refractive index of the environment in the immediate vicinity of the surface of the diffraction element 601. Thus, the resulting diffraction pattern projected onto the image sensing detector 650 changes its shape when the refractive index in the vicinity of the diffraction element 601 changes. The bottom of the sample holder 640 is constituted at least in part of the metal layer 602 or diffraction pattern 601 so that the surface of the diffraction element 601 is configured to interact with the solution in the sample holder 640. The metal layer or diffraction pattern may be coated with a coating which may be a protective coating, which may serve to prevent direct contact between the solution and the metal or diffraction pattern, while allowing for near field interaction between the metal or diffraction pattern and moieties in the solution. Because the target substance 609 has a refractive index that differs from the refractive index of the solution, when the target substance 609 in the solution is attached or associated with the diffraction element 601 (see FIG. 6B), the refractive index in the vicinity of the diffraction element 601 changes, and the change in refractive index is in turn detectable by a spatial position shift, for example, of the diffraction pattern projected onto the image sensing detector 650.

When the openings in the diffraction element 601 are to be filled with a dielectric, the dielectric can be made of silicon oxide or any other material transparent to the incident light, for example. The metal layer 602 is made of a material that can support at least some generation and propagation of plasmon waves, such as aluminum, copper, ruthenium, rhodium, palladium, silver, osmium, iridium, platinum, and gold, or any alloy thereof as well as any other suitable conductive and reflective material or the like.

In this embodiment, a two-dimensional spatial change in the diffraction pattern 607 that results from the change in refractive index is measured by the image sensor 650 having numerous pixels 606. For some combinations of the target substance 609 and diffraction elements, the spatial pattern change may be an expansion, contraction, or shift of the overall two-dimensional diffraction pattern projected onto the image sensing detector 650 in a ratio roughly proportional to the change in the refractive index. FIG. 6B schematically illustrates in an exaggerated manner a shrinkage of the diffraction pattern 607 in response to the arrival of the target substance 609 as an example.

Furthermore, the diffraction element 601 and the image sensing detector 650 may be configured and arranged such that the resulting diffraction pattern 607 on the image sensing detector 650 exhibits a plurality of distinct diffraction spots or lines so that the pattern change can be readily detected and recognized by a relatively inexpensive image sensor having a sufficient spatial resolution.

Whether spots or lines are adequately distinct depends on the spatial resolution and the intensity resolution of the image sensing detector 650. For example, when a relatively simple image sensor having a low-intensity resolution, but a high pixel density, is used, spots or lines may be determined to be sufficiently distinct when the pixels of the image sensing detector 650 register more than about 30% intensity drop over a few pixels or a few tens of pixels across darker areas between the adjacent spots or lines. When an image sensing detector 650 with a high intensity resolution is used, a much smaller change in the intensity of the received light can be recognized as distinct spots or lines. In determining these intensity variations, a bright spot(s) that is not much affected by the refractive index change of interest (typically a bright spot at the center of the diffraction pattern 607) may be disregarded by ignoring pixels detecting the bright spot(s) and/or by adjusting the range of the intensities each pixel can resolve. Alternatively, such a spot(s) may be blocked by a light shielding pattern formed on the image sensing detector 650, for example. Alternatively, the image sensing detector 650 (or multiple image sensors) may be placed such that only select features of the diffraction pattern 607 are detected. These distinct spots or lines may constitute key features of the diffraction pattern 607, which can be used to identify the pattern and detect small changes in the diffraction pattern 607. For example, an overall arrangement of respective peak positions of the key features can be detected and recognized using a relatively simple data processor and algorithm for pattern recognition. Relative positions among a plurality of select features in the diffraction pattern 607 (like spots or lines) can be detected and the changes thereof can be evaluated to determine the presence or absence of the target substance 609.

In this embodiment, substantially monochromatic light 603 may have a central wavelength of 200 nm to 1100 nm, for example. Diffraction element 601 may have a detection site, which is sensitive to a refractive index change, in lateral dimensions in the range of 5 to 50 microns, for example. An example of the detection site is depicted by the rectangular box 601 indicated in FIG. 6A. The distance h between the diffraction element 601 and the image sensor 605 may be 0.05 mm to 10 mm or more, for example, to ensure development of the diffraction pattern on the image sensor.

Returning to FIGS. 6A and 6B, in this embodiment, the change in the diffraction pattern is detected by the image sensing detector 650 having numerous pixels 606. Specifically, a processor 670 is connected to the image sensing detector 650 to process signals from the image sensor so that the processor 670 can determine the change in the diffraction pattern 607—hence, the presence or absence of the target substance. Alternatively, the processor 670 may be designed to conduct only portions of the signal processing, such as A/D conversion and addressing, and may forward the processed data to a host computer/device for further processing for the determination of the pattern change and the presence of the target substance. The processor 670 may be equipped with user programmable FLASH or like memory to store software for executing pre-installed algorithms to perform the data processing. In addition, drivers or other circuits are provided to drive the image sensing detector 650 and light source 608, and to extract signals representing the light intensity received at the image sensing detector 650.

Various data processing methods can be used to process signals from the image sensing detector 650. For example, the processor or the host computer connected to the processor 670 may use a single threshold to determine the presence or absence of the target substance on the surface when a relatively large change in refractive index is to be detected.

The processor 670 or the host computer may process the data to detect a pattern formed by at least some of the plurality of distinct diffraction spots or lines in the diffraction pattern, and determines the presence or absence of the target substance in accordance with a two-dimensional spatial change in the pattern. Furthermore, alternatively or in addition, the processor 670 or the host computer may use a subpixel interpolation algorithm to determine two-dimensional coordinates representing a position of at least one of a plurality of distinct diffraction spots or lines when the diffraction pattern contain such a plurality of distinct diffraction spots or lines. The processor 670 or the host computer may use a subpixel interpolation algorithm to determine two-dimensional coordinates representing respective peak positions of a plurality of distinct diffraction spots or lines at a resolution greater than a resolution of the image sensor, and may detect a pattern formed by the determined peak positions of the plurality of distinct diffraction spots or lines using a pattern recognition algorithm, and the processor 670 or the host computer then may determine the presence or absence of the target substance in accordance with a two-dimensional spatial change in the pattern.

In a further embodiment, the grating or prism may be manually or automatically adjustable, and a manually or automatically adjustable slit may be provided such that a wavelength and bandpass may be manually or automatically adjusted. In some embodiments, selected wavelengths and band passes may be utilized as part of an automated protocol. In yet further embodiments, a continuous scan over a range of wavelengths may be automatically performed, permitting the generation of a continuous data set of absorption as correlated with time and wavelength. In further embodiments, a dual monochromator with adjustable gratings may be utilized so as to provide for tunable near monochromatic light.

In some embodiments, the intensity of the light source(s) may be varied. In some embodiments, the source may be pulsed or chopped as with an optical chopper. The frequency and duty cycle of the chopped or pulsed light source may be varied for different diffraction elements, or may be varied during the use of one or more diffraction elements for one or more assays, and may be effectively nonvariable during an assay, or may be varied during an assay.

In some embodiments, a light source may have a particular angle of incidence with respect to the diffraction elements instead of a normal direction as in the embodiments described above. The angle of incidence may be different for different light sources when the system has more than one light source, or may have different particular angles of incidence for different diffraction elements.

In some embodiments, a light source may be configured such that the angle of incidence with respect to the diffraction element may be changed. Said change may be made manually, by rotating a light source and or a portion of the light path and associated optical elements pivotably about the optical center of the diffraction element, wherein after said rotation, a pin or screw mechanism may be utilized to hold a light source stably in place relative to the diffraction elements. In other embodiments, said rotation may be effectuated in an automated manner, such as by a linear or rotary actuator.

In some embodiments, said rotation of a light source may affect the rotational relationship between the diffraction element, whilst the angle of incidence may be maintained. The change may be made manually, by rotating a light source and or a portion of the light path and associated optical elements pivotably about the optical center of the diffraction element, wherein after the rotation, a pin or screw mechanism may be utilized to hold a light source stably in place relative to said plasmonic filter. In other embodiments, said rotation may be effectuated in an automated manner, such as by a linear or rotary actuator. Rotation of a light source may affect both the angle of incidence of the light source with respect to the plasmonic filter, and the rotational relationship between the light source and the plasmonic filter. One or both rotations may be manual or automated, or one may be manual whilst the other is automated.

More than one light source may be utilized, with light intensity of various light sources being adjusted to increase or decrease by use of an optical chopper, by raising and lowering the current to a LED or laser diode, or by the use of a shutter, which may be an electronic shutter, such as an LCD shutter. The sources may be separated by wavelength, such as when different laser diodes are utilized as different sources, or when different filters are used for different or the same light source(s). The sources may be separated by being of different polarizations as described hereinafter. The sources may be separated by having different angles of incidence with respect to the plasmonic filter in one or both axis. Combinations of the above may be utilized such as turning on and off different light sources at different times, which are further separated by having different wavelengths. Any combination of time separation of light sources, spatial separation of light sources, wavelength separation of light sources, polarization separation of light sources, and angles of incidence with respect to the plasmonic filter in one or both axis may be combined.

In still other embodiments the light source 608 may turned on and off at different times at different portions of a two dimensional array of plasmonic filters, creating a spatial light pattern. The spatial light pattern may be generated by imaging a two dimensional OLED array onto the two dimensional array of plasmonic filters wherein different elements the two dimensional array of OLEDs may be modulated individually or in groups or sets so as to create a spatial light pattern at the two dimensional plasmonic filter array. In another embodiment, a two dimensional digital micromirror device (DMD) may be imaged onto the two dimensional array of plasmonic filters may be generated by imaging wherein different elements of the two dimensional array of DMDs may be controlled so as to be modulated individually or in groups or sets of light so as to create a spatial light pattern at the two dimensional plasmonic filter array.

A collimation element may be required if light from light source is not sufficiently collimated. Use of a collimation element may be preferred when the light source is an LED or a laser diode. A LED collimator may comprise, at least in part, a reflector. In some embodiments, a LED collimator may at least in part comprise an aspheric or Fresnel lens or lens system. In some embodiments, a laser collimator may also comprise a beam expander such as a 5× or 10× beam expander.

In some embodiments, the solution may be introduced on the sensor side of the diffraction element. In this case, incident light would interact first with the diffraction element, then the solution, before being detected by the image sensor. Changes in the diffraction patterns produced in these embodiments would be detectable in the same manner as described previously. Additional scattering at the solution/camera interface may occur with this arrangement, though scattering at the light source/solution interface is eliminated. The noise reduction techniques described above or those known in the art may be employed to improve the S/N ratio.

As will be understood, filters, collimators, light guides or other intermediary optical components may be constructed using commercially available glasses or polymers. Specialty glasses may be required for certain embodiments requiring transmission of ultraviolet wavelengths. This is particularly true for when it is desirable to use wavelengths between 200 nm and 400 nm, and wherein it may be desirable to utilize transmissive optical elements. In other embodiments, a glass such as a zinc barium silicate glass or a borosilicate float glass may be utilized. In further embodiments, wherein a desired wavelength may be 350 nm or more, a standard soda lime glass may be utilized.

In some embodiments, it may be desirable to utilize reflective optics rather than refractive optics, particularly when the desired wavelength is below 350 nm, and even more particularly when the desired wavelength is below 300 nm. Thus any focusing optics and/or filters may be configured as mirrors rather than as transmissive elements, so as to prevent the need (and cost) of fused silica. In other embodiments, fused silica may be utilized for transmissive elements.

The diffraction element can include a structurally patterned metal film composed in whole or in part of gold, silver, copper, aluminum, or alloys thereof, as well as any other suitable conductive and reflective material. Multiple different metals or metal alloys may be utilized in different areas of the plasmonic filter elements. Metamaterials such as aligned microwires, such as aligned silver, aluminum or gold nanowires may be utilized, and may be further formed into plasmonic filter elements. Other materials such as those considered to be dielectrics may be utilized either with or without metals.

The diffraction elements may have a compact mosaic, loose tile pattern, a rectangular or other grid layout, or circular, arcuate, spiral, or other desired geometric shape. Each diffraction element may have nanoscale patterning of metallic and dielectric shapes that selectively inhibit or promote transmission of various wavelengths of light therethrough. In certain embodiments, diffractive elements can be formed from holes (including arrays of holes) in a metal film, by scattering occlusions in transparent films, apertures filled with a transparent dielectric in a metal film, or dielectric particles in a regular or irregular distribution on a surface. The apertures or holes in a metal film may completely penetrate the metal film, or may partly penetrate the metal film, or some apertures or holes may fully penetrate the metal film, and other apertures or holes may partially penetrate the metal film. These plasmonic structures, which can include upraised structures, islands, and open or dielectric filled apertures, may be configured such that the incident light may be resonant with at least one plasmon mode on the surface of the structures in said metal film or metal islands, and the metallic plasmonic structures provide surface plasmon energy resonance bands for the wavelength selective transmission of light. In alternate embodiments, concentration of electromagnetic fields in a surface plasmonic process could be used to enhance intensity-dependent processes such as upconversion or two photon events.

The diffraction elements may include one or more array patterns, with each array pattern being defined with the design rule which determines the long range order of the filter. The array may be periodic, aperiodic, quasi-periodic, and may be laid out in one, two, or three dimensions. The periodicity may be different in the different dimensions or in different layers for multilayer embodiments. The array pattern primarily determines the surface wave interference properties, and secondarily influences the scattering and coupling behavior of neighboring elements through mutual electromagnetic dipole interaction. The motif describes the detailed geometry of the constituent elements in the array. The shape and material composition of the motif elements primarily determine the optical scattering spectrum and strength. Examples of motif elements include holes (including arrays of holes) in a metal film, scattering occlusions in transparent films, complex apertures such as coaxial holes, and dielectric or metal particles in a regular or irregular distribution on a surface.

Radial symmetries utilizing any of the aforementioned apertures or combinations thereof may be utilized. The combinations may be configured to provide a single effective wavelength with greater sensitivity, or may be configured to provide multiple wavelengths to be associated with a single "micro spectrometer", or a combination thereof may be utilized.

In some embodiments, a motif or feature of the diffraction element will be characterized by a complete removal of material from some fraction of the plane (binary motifs) whereas in other embodiments a motif may describe a more complex pattern with varying thickness or composition. In some embodiments, a motif or feature of the diffraction element may be a circular aperture from which material is removed completely, or a motif may be a circular aperture from which material is removed incrementally in order to form an inverted cone structure. Motifs can therefore be described by a two dimensional function f(x,y) corresponding to the process conditions at each point. For example, a function may correspond to the fractional removal of material, the fractional overcoating of material with a second material, the fractional implantation of a material with a dopant or other modifying material, or the variation in porosity of a material.

The image sensors that can be used include any focal plane array (FPA) device, including a front or back illuminated charge-coupled device (CCD), a photon penetration depth dependent device, a photo-diode array (PDA), an avalanche photodiode (APD) array, a PMT array, or a front or back illuminated complementary metal-oxide semiconductor (CMOS) detector. For low cost embodiments, as described above, consumer CMOS detectors can be used with suitable modifications. Preferably, such detectors will have a pixel count in excess of the number of diffraction elements in a multi-detection system described above, and may be a multiple of the number of diffraction elements, such as 10 times, 100 times, or 1000 times as many pixels as diffraction elements, with an a sensor area quantum efficiency of from 10% to 90% depending on wavelength and whether the detector is a front side illuminated or backside illuminated device, a read noise of from 0.2 to 40, or 1 to 10, or 2 to 6 electrons, and read-out speed of from 1 to 1000, or from 10 to 100 full frames per second. Alternatively, a CCD chip can be used for applications requiring greater count accuracy, quantum yield, and binning flexibility. The sensor may be cooled or temperature stabilized. The sensor may be a monolithic sensor, or may be a hybrid sensor with different sections of the sensor utilizing different materials (such as silicon, InGaAs, HgCdTe), such that the different sections may have different wavelength quantum efficiencies, or the sensor may be a sensor assembly wherein multiple sensor chips may be integrated into a single sensor, which may be effectuated utilizing a PCB or hybrid assembly. Monochrome detectors can be used, or alternatively, detectors with conventional Bayer filters or other custom absorption, dielectric or polarization filters can be used.

In some embodiments, the image sensor may utilize 10 bit data acquisition, or may utilize an A/D converter with higher sensitivity, such as a 12 bit, 14 bit or 16 bit A/D converter. In other embodiments, a sensor may be utilized which utilizes an electron multiplying CCD sensor, which may have a read noise of less than one photoelectrons.

In some embodiments wherein a CMOS image sensor is utilized, and a maximum image throughput (maximum frame rate) is desired, a rolling shutter readout of the CMOS sensor may be performed. In other embodiments, wherein a CMOS image sensor is utilized and it is desired that readout of different portions be very well synchronized with each other, a global readout of the CMOS sensor may be performed.

In some embodiments, a separate photodiode reference may be utilized in addition to the "main" image sensor. Said diode may be utilized as a reference level in order to set the effective input power level, either by setting the "main" sensor integration time, or by setting the size of one or more of the input apertures for a sunlight input system, or by setting the power level of a LED, laser, or other power supply, or a combination of setting the integration time/aperture and or light source power level.

In some embodiments, to minimize the thickness of the device, the plasmonic structure may be directly fabricated on top of a CMOS sensor with a flat transparent spacer/protective layer in between. The advantage of such a system is that the exact distance between the plasmonic structure and the detector surface can be precisely controlled by defining the deposition thickness of the transparent spacer via magnetron sputtering or plasma enhanced chemical vapor deposition (PECVD) or pulsed laser deposition. This enables accurate determination of the magnification factor and the conversion between the detected diffraction pattern image and the scattering angular distribution. The spacer thickness may be thick enough such that there may be sufficient magnification of the diffraction pattern on the sensor surface. In some embodiments, a single diffraction feature (peaks, troughs or inflection points) may have a spatial extent of several detector pixels so that sub-pixel averaging is possible for high sensitivity tracking of pattern changes. However, the separation between the diffraction element and the detector cannot be too large otherwise the sensitivity of nearby sensing regions will be reduced due to cross-talk (in this case, large angle diffraction from one sensing region may be detected by an adjacent region).

In some embodiments, additional micro-lenses (~100 microns or smaller) can be integrated with the detection sensor or with the output surface of the diffraction element to increase the angular spread of the diffraction pattern for enhanced resolution (higher angular magnification) or reduce the angular spread of the diffraction pattern to minimize cross-talk between adjacent sensors for higher integration density. For example, by placing a total internal reflection lens (TIR lens) over the output surface of the diffraction element, large angle scattering will be reflected towards the normal direction, thus eliminating their interference with adjacent sensor regions, enabling high-density integration of sensing regions while conserving the total number of diffraction features for parallel information. Other dielectric optical elements may be inserted between the diffraction element and the detector to engineer the scattering angular distribution from the diffraction element. Filtering of the scattering angular distribution can also be accomplished by a secondary plasmonic filter alone or in combination with a lens or aperture which may serve to block one or more of the orders of the spectrum which may be transmitted by said plasmonic filter. In some embodiments, it may be particularly desirable to block zero order light, as it may not have appropriate spectral dispersion. In some embodiments, more light may be present in zero order than in first order light, potentially causing saturation of a sensor. It may further be desirable to block second order or higher light, while passing first order light. Such a block may be a physical aperture.

In operation, differences in refractive index in the immediate vicinity of a diffraction element are measured. The change in refractive index may result from changes in the refractive index of the bulk solution, or may result from binding events, particularly binding events which occur between moieties in solution and moieties bound to or immediately adjacent to the diffraction element (i.e., surface-immobilized receptors). For purposes herein, immediately adjacent or vicinity may mean within a distance equal to two times the wavelength of light. Binding may change the refractive index of the area in the immediate vicinity of a plasmonic filter element. Binding can include various chemical or biological molecules of diagnostic interest, including but not limited to antigen antibody binding, DNA hybridization, RNA DNA hybridization, aptamer binding, binding of organic molecules, or metals, binding of a protein or enzyme to a DNA or RNA molecule, or the formation of a self-assembled monolayer.

The detection mode conducted by the processor or the host device connected to the processor may include the steps of identifying intensity peaks in the diffraction image, locating them relative to the camera pixel positions, and tracking any motion of such peaks (for example, in i,j pixel space) actuated by the presence/absence of analyte. Assuming that the typical size of these peaks is about 1/10 of the total image size or smaller, the device may be tracking features that may be only a few times the size of a camera pixel. Software processing may be employed to achieve enhanced subpixel resolution through peak fitting or other suitable image processing techniques. Efficient autocorrelation may also be performed by processing in the frequency domain using Fourier transform techniques. In particular, autocorrelation may be combined with an optimization over a subpixel image shift parameter controlling a linearly varying phase term applied to the frequency representation of the image prior to multiplication in the frequency domain.

Due to the mode of operation of this device, in some embodiments, the detection may be made relatively insensitive to variation in the source power. In an alternate implementation, the illumination could be several independent monochromatic coherent light sources. Multiple color channels provide extra data, which increases the overall selectivity of the device. Advantageously, this type of implementation may take advantage of color detectors having a conventional Bayer filter pattern. In addition, plasmonic surfaces can be designed to generate distinct diffraction response at each illumination color and multi-color channel data analysis can be used to improve effective detection sensitivity.

Figure 7:
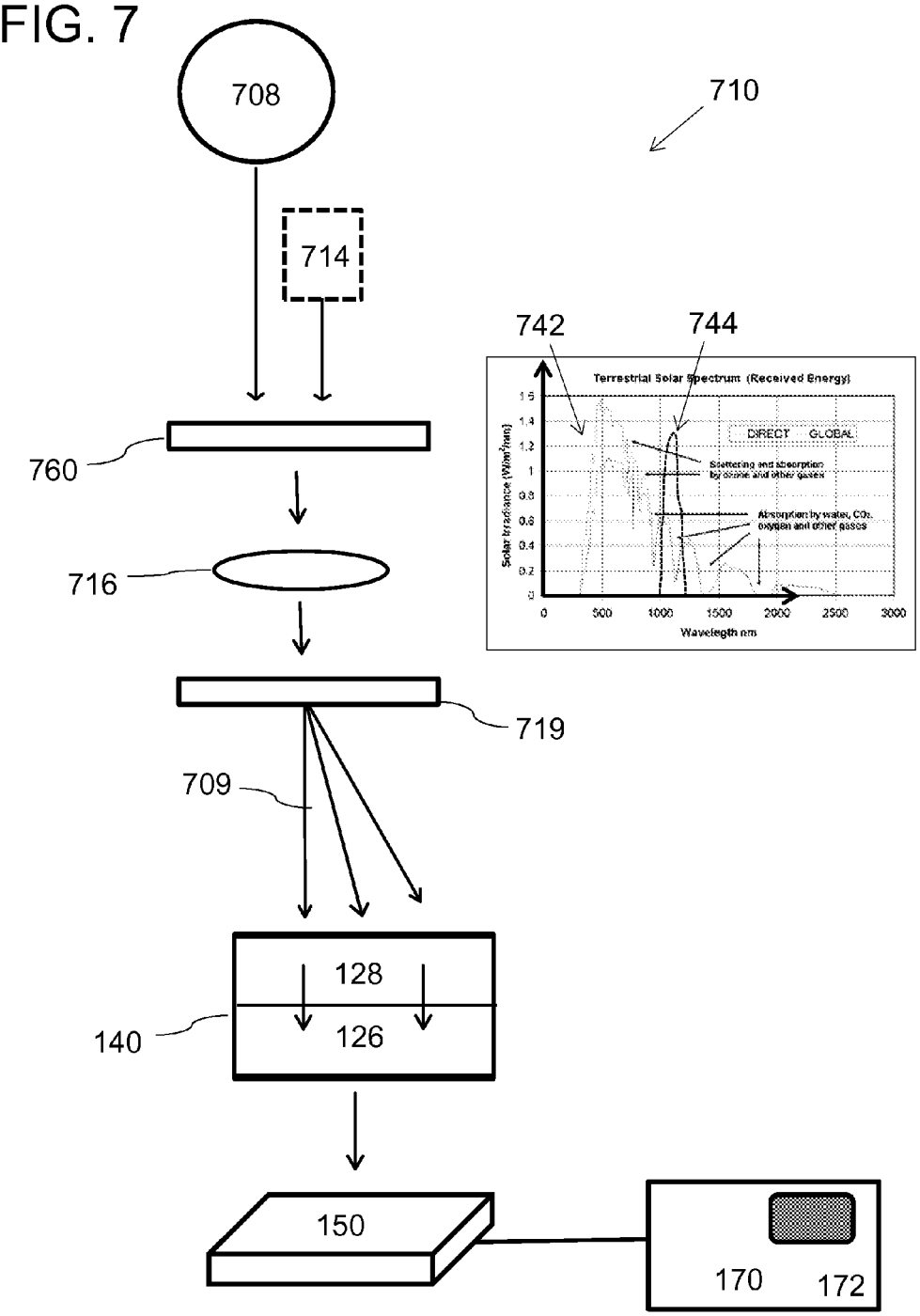
FIG. 7 is a view of a simultaneous full spectrum monitoring hand holdable spectrometer.

FIG. 7 illustrates a simultaneous full spectrum spectrometer system 710 including an ambient light source 708, an optional aperture 760, an optional auxiliary light 714, collimation optics 716, sample holder 740, transmission grating 719, and detector 750.

Incoming light from a full spectrum ambient light source 708 such as the sun may be collimated by collimation optics prior to being spectrally spread by a transmission grating 719, prism, or reflecting grating or other optical element capable of spectrally spreading the input full spectrum light to form spectrally dispersed light 709. The spectrally spread light 709 may then interact with an analyte sample 728 and or control sample 726 held in a sample container 740 or present on a reflective surface, before being detected by a detector 750. The detector 750 is connected to control electronics 770 for system control, data analysis, and result output potentially using optional display 772. In disclosed embodiments, ambient light, which may be solar light having a spectrum 742 is the light source, but selected wavelengths of light can be added to provide greater intensity at selected peaks (e.g. peak 744). Ambient light source 708 can include sunlight, some discharge lamps such as xenon or deuterium, incandescent lamps, halogen lamps, fluorescent lamps, or white LEDs. In some embodiments, a lamp with multiple line spectra such as a mercury arc lamp may be utilized.

In addition to ambient light, other optional auxiliary light source(s) 714 can be used to selectively intensify selected wavelengths or provide additional wavelengths not available in the ambient light source 708 such that any wavelengths which have insufficient illumination from the ambient light source 708 may be spectrally "filled in" so that all desired wavelengths are present and may simultaneously illuminate the analyte sample 728 and or control sample 726 and detector 750. Areas of the detector 750 associated with appropriate areas of the control sample 726 further associated with desired wavelengths may be utilized to insure that sufficient light is present for all desired wavelengths, while the corresponding areas of the detector 750 associated with the appropriate areas of the analyte sample 728 are simultaneously monitored. The processor 770 may normalize the signal levels associated with the corresponding control sample 726 and analyte sample 728 and display results on the optional display 772.

Traditionally, bulky and expensive optical detection/measurement apparatus (such as spectrometer, diffraction apparatus, Biacore systems) required a designated light source and optical components as the probing light. Versatility and high-precision requirements of those devices need such sophisticated light source/optical components in order to control and adjust various optical properties of the probing light that interacts with the analyte or medium of interest. Typically, various stringent requirements must be met for the light sources/optical components.

In the advent of personalized healthcare and distributed diagnosis, portable diagnostic or measurement devices are in much need. For these devices, instead of the versatility and high-precision requirements, what are sought after are reliable and convenient detection schemes and less complex mechanisms for particular sets of target substances/analytes. In this regime, optical measurement/detection devices are of particular interest. Such optical devices may detect the target substances by way of absorption spectroscopy or by measurement of refractive index changes, for example, that occur as a result of the presence of the analyte or interactions with the analyte.

The recent advancement of plasmonics technologies has made it possible to construct various optical measurement devices that can be configured to meet the requirements of portability, reliability, and convenience, as disclosed in commonly owned, concurrently filed PCT International Application Nos. PCT/US2013/072927 and PCT/US2013/072930, both designating the U.S., respectively entitled "Cuvette For Spectroscopic Sensor and Cuvette" and "Plasmonic Projected Diffraction Sensor", respectively claiming the benefit of Provisional Applications Nos. 61/734,934, filed Dec. 7, 2012, and 61/762,818, filed Feb. 8, 2013. These International Applications PCT/US2013/072927 and PCT/US2013/072930 are hereby incorporated by reference in its entireties.

For at least some of these portable devices, the required optical properties of the probing light significantly overlap or otherwise are satisfied by the optical properties of certain types of ambient light (such as sunlight, moonlight, commercial light for room illumination and scattered light from these sources). As described above, ambient light can be used as is, or can be optically processed within the device to be used as the probing light for the devices.

As described above, some of the optical properties (spectrum, bandwidth, coherence, collimaticity, intensity, etc.) of ambient light significantly vary from time to time and among the types of ambient light. For example, the sunlight has a wide range of variations in its optical spectrum and intensity, depending on the weather condition, humidity, time of the day, or altitude. Lighting devices for room illumination have a wide range of different spectrums and intensities, depending on the light bulb they use.

As described above, in one aspect, the present invention provides various mechanisms for appropriately utilizing ambient light in portable, optical measurement devices. Using ambient light (plus an optional augmenting internal light source) is cheaper and more power efficient, which allows for better portable spectroscopy devices for field deployment. As described above, multi-channel spectroscopy devices can be built to measure the illumination characteristics of the ambient light used at the same moment as the sample to be measured is observed. Multichannel devices can be constructed such that some channels are used as passthrough filters so that the variation in ambient light can be taken into account in real time. For example, as described above, in some embodiments, null or control sample 126 is juxtaposed with the analyte sample 128 in the sample folder 140. See FIG. 1, for example. By analyzing differentials of signals from the detector 150 that represent differences in the detected intensities between the analyte sample 128 and the control sample 126, any variations of the light impinging upon the sample holder 140 can be reliably taken into account. In other words, the detection signals from the analyte sample 128 may be normalized by the detection signals from the null or control sample 126 in real time to eliminate the fluctuation effects of the light. Such differential data processing can be implemented by appropriate software or hardware. If the differential data processing/normalization does not yield a sufficient signal-to-noise ratio (SNR) (with adjustment of some optical components or the orientation of the device, as described above), the light may be supplemented by an optional auxiliary light 114 of FIG. 1), or the results may be rejected as insufficient and the user can be alerted, as described above. It will be apparent to those skilled in the art that various modifications and variations can be made without departing from the spirit or scope of the invention. Thus, it is intended that the disclosed embodiments cover modifications and variations that come within the scope of the claims that eventually issue in a patent(s) originating from this application and their equivalents. In particular, it is explicitly contemplated that any part or whole of any two or more of the embodiments and their modifications described above can be combined in whole or in part.

What is claimed is:

1. A device for detecting a target substance in a solution, comprising:
    a light source that processes and filters the ambient light to emit substantially monochromatic light;
    a sample container configured to contain the solution that contains one or more types of target substances, said solution having a refractive index different from a refractive index of said one or more types of target substances;
    a reference container containing no substance therein or a reference for the target substances;
    a substantially planar diffraction element optically coupled to the light source to receive the light originating from the light source, the diffraction element having a top surface and a bottom surface and having one or more of openings that are empty or filled with a dielectric to generate plasmon waves upon receipt of the light from the light source, the top surface of the diffraction element being configured to be in contact with the solution in the sample container and with the reference container and configured to be chemically treated to attach surface-immobilized receptors thereon that will bind said one or more types of target substances in the solution so that a change in refractive index occurs in the vicinity of said top surface when the target substance binds to said top surface;
    a two-dimensional image sensor disposed under the diffraction element to detect a first diffraction pattern projected onto the two-dimensional image sensor by the light from the light source that has interacted with a portion of the diffraction element that is in contact with the solution in the sample container and to detect a second diffraction pattern projected onto the two-dimensional image sensor by the light from the light source that has interacted with another portion of the diffraction element that is in contact with the reference container, the two-dimensional image sensor having a plurality of pixels to detect the diffraction patterns; and
    a processor connected to the two dimensional image sensor to process signals representing the first diffraction pattern with signals representing the second diffraction pattern, outputted from the two-dimensional image sensor, so as to compensate for fluctuations of said ambient light for determining the presence or absence of the target substance on the diffraction element,
    wherein the diffraction element and the two-dimensional image sensor are configured and arranged such that, upon receipt of the light from the light source, the plasmon waves are generated on the diffraction element so as to generate the diffraction pattern that includes a plurality of distinct diffraction spots or lines on the two-dimensional image sensor, properties of which are dependent on the refractive index in the vicinity of the top surface of the diffraction element.

2. The device according to claim 1, wherein the diffraction element and the two-dimensional image sensor are configured and arranged such that said change in refractive index that occurs when the target substance binds to the top surface of the diffraction element causes at least one of the plurality of diffraction spots or lines to shift its position by a distance greater than a pitch of the pixels.

3. The device according to claim 1, wherein the device is configured to detect a single target substance and the processor uses a single threshold to determine the presence or absence of the target substance on the surface of the top layer of the diffraction element in processing signals from the image sensor.

4. The device according to claim 1, wherein the processor processes the signals from the two-dimensional image sensor to detect a pattern formed by at least some of the plurality of distinct diffraction spots or lines, and determines the presence or absence of the target substance in accordance with a two-dimensional spatial change in the pattern.

5. The device according to claim 1, wherein the processor uses a subpixel interpolation algorithm to determine two-dimensional coordinates representing a position of at least one of the plurality of distinct diffraction spots or lines.

6. The device according to claim 1, wherein the processor uses a subpixel interpolation algorithm to determine two-dimensional coordinates representing respective peak positions of the plurality of distinct diffraction spots or lines at a resolution greater than a resolution of the two-dimensional image sensor, and detects a pattern formed by the determined peak positions of the plurality of distinct diffraction spots or lines using a pattern recognition algorithm, and wherein the processor determines the presence or absence of the target substance in accordance with a two-dimensional spatial change in the pattern.

7. The device according to claim 1, wherein the diffraction element has a detection site defined by a two-dimensional area on the top surface thereof that includes said one or more of openings and a vicinity thereof, and wherein when the target substance covers only partially the detection site of the diffraction element, the processor processes the signals from the image sensor to determine an area percentage at which the target substance occupies the detection site.

8. The device according to claim 1, wherein the light emitted from the light source is directed to the sample container so that the light passes through the sample container containing solution to interact with the diffraction element.

9. The device according to claim 1, further comprising an optical modulator that modulates at least one of phase, polarization, and intensity of the light emitted from the light source, wherein the processor demodulates the signals from the image sensor to improve a signal-to-noise ratio.

10. The device according to claim 1, further comprising a polarizer to polarize the light emitted from the light source so that the light impinging upon the top surface of the diffraction element is linearly polarized.

11. The device according to claim 1, wherein the diffraction element is made of a metal and the opening is filled with a dielectric.

12. The device according to claim 1, wherein the diffraction element has a periodic array of a plurality of the openings.

* * * * *